(12) United States Patent
Gu et al.

(10) Patent No.: US 6,624,184 B1
(45) Date of Patent: Sep. 23, 2003

(54) AMIDE AND DIAMIDE INHIBITORS OF IMPDH ENZYME FOR USE IN TREATING IMPDH-ASSOCIATED DISORDERS

(75) Inventors: Henry H. Gu, Bordentown, NJ (US); T. G. Murali Dhar, Newtown, PA (US); Edwin J. Iwanowicz, Cranbury, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/427,953

(22) Filed: Oct. 27, 1999

Related U.S. Application Data
(60) Provisional application No. 60/106,180, filed on Oct. 29, 1998.

(51) Int. Cl.⁷ .................... A61K 31/421; A61K 31/422; C07D 263/33; C07D 413/12
(52) U.S. Cl. ................. 514/374; 548/235; 548/236; 560/43; 560/45; 564/160; 564/168; 564/169
(58) Field of Search ............................... 548/236, 235; 560/43, 45; 564/160, 168, 169; 514/374

(56) References Cited

U.S. PATENT DOCUMENTS

| | | | | |
|---|---|---|---|---|
| 2,239,440 A | * | 4/1941 | D'Alelio ................. 564/160 X |
| 2,304,820 A | * | 12/1942 | Hanford et al. ............... 560/43 |
| 2,464,597 A | * | 3/1949 | McQueen ................ 564/169 X |
| 2,742,502 A | * | 4/1956 | Crowe et al. ............. 560/43 X |
| 3,254,108 A | * | 5/1966 | Maggiulli et al. ........ 560/43 X |
| 3,317,584 A | * | 5/1967 | Stoffel ...................... 560/43 X |
| 3,318,842 A | * | 5/1967 | Blachere et al. .......... 560/43 X |
| 3,511,804 A | * | 5/1970 | Duennenberger et al. . 560/43 X |
| 3,711,509 A | * | 1/1973 | Weber et al. ............. 560/43 X |
| 3,906,033 A | * | 9/1975 | Biland et al. ........... 564/160 X |
| 3,966,965 A | * | 6/1976 | Sellstedt et al. ............. 424/309 |
| 4,119,783 A | * | 10/1978 | Hall et al. ..................... 560/43 |
| 4,228,082 A | * | 10/1980 | Kleemann et al. ....... 564/169 X |
| 4,686,234 A | | 8/1987 | Nelson et al. ............... 514/374 |
| 4,725,622 A | | 2/1988 | Nelson et al. ............... 514/469 |
| 4,727,069 A | | 2/1988 | Nelson et al. ............... 514/211 |
| 4,753,935 A | | 6/1988 | Nelson et al. ........... 514/233.5 |
| 4,786,637 A | | 11/1988 | Allison et al. ........... 514/233.5 |
| 4,808,592 A | | 2/1989 | Nelson et al. ........... 514/233.5 |
| 4,861,776 A | | 8/1989 | Nelson et al. ........... 514/233.5 |
| 4,861,791 A | | 8/1989 | Diana et al. ................. 514/374 |
| 4,868,153 A | | 9/1989 | Allison et al. ............... 514/470 |
| 4,948,793 A | | 8/1990 | Allison et al. ........... 514/233.5 |
| 4,952,579 A | | 8/1990 | Nelson et al. ........... 514/233.5 |
| 4,959,387 A | | 9/1990 | Nelson et al. ............... 514/469 |
| 4,992,467 A | | 2/1991 | Allison et al. ............... 514/464 |
| 5,073,562 A | | 12/1991 | Djuric et al. ................ 514/365 |
| 5,247,083 A | | 9/1993 | Knox et al. .................. 544/153 |
| 5,334,604 A | | 8/1994 | Goldstein et al. ........... 514/364 |
| 5,369,108 A | * | 11/1994 | Breslow et al. ............. 514/266 |
| 5,380,879 A | | 1/1995 | Sjogren ...................... 549/310 |
| 5,444,072 A | | 8/1995 | Patterson et al. ........... 514/320 |
| 5,665,583 A | | 9/1997 | Collart et al. ................ 435/191 |
| 5,807,876 A | | 9/1998 | Armistead et al. .......... 514/374 |

FOREIGN PATENT DOCUMENTS

| | | | |
|---|---|---|---|
| EP | 1127883 A2 | | 8/2001 |
| JP | 40-104 | * | 1/1940 |
| JP | 58-150548 | * | 9/1983 |
| JP | 6-306036 | * | 11/1994 |
| WO | WO94/01105 | | 1/1994 |
| WO | WO94/12184 | | 6/1994 |
| WO | WO97/40028 | | 10/1997 |
| WO | WO98/40381 | | 9/1998 |
| WO | WO99/55663 | | 11/1999 |

OTHER PUBLICATIONS

Nature 256:331–333 (1975) Jackson et al.
J. Biol. Chem. 263:15769–15662 (1988) Collart et al.
J. Biol. Chem. 265:5292–5295 (1990) Natsumeda et al.
J. Biol. Chem. 266:506–509 (1991) Weber.
J. Biol. Chem. 268:27286–27290 (1993) Carr.

* cited by examiner

*Primary Examiner*—Laura L. Stockton
(74) *Attorney, Agent, or Firm*—Laurel Lee Duncan; Audrey Sher; Maureen P. O Brien

(57) ABSTRACT

The present invention discloses the identification of the inhibitors of IMPDH (inosine-5'-monophosphate dehydrogenase). The compounds and pharmaceutical compositions disclosed herein are useful in treating or preventing IMPDH associated disorders, such as transplant rejection and autoimmune diseases.

19 Claims, No Drawings

AMIDE AND DIAMIDE INHIBITORS OF IMPDH ENZYME FOR USE IN TREATING IMPDH-ASSOCIATED DISORDERS

This application claims priority from provisional U.S. application Ser. No. 60/106,180, filed Oct. 29, 1998, which is incorporated herein by reference in its entirety.

FIELD OF THE INVENTION

The present invention relates to novel compounds which inhibit IMPDH. The invention also encompasses pharmaceutical compositions comprising these compounds. The compounds and pharmaceutical compositions of the invention are particularly well suited for inhibiting IMPDH enzyme activity and, consequently, may be advantageously used as therapeutic agents for IMPDH-associated disorders. This invention also relates to methods for inhibiting the activity of IMPDH using the compounds of this invention and related compounds.

BACKGROUND OF THE INVENTION

Inosine monophosphate dehydrogenase (IMPDH) has been shown to be a key enzyme in the regulation of cell proliferation and differentiation. Nucleotides are required for cells to divide and replicate. In mammals, nucleotides may be synthesized through one of two pathways: the de novo synthesis pathway or the salvage pathway. The extent of utilization of each pathway is dependent on the cell type. This selectivity has ramifications with regard to therapeutic utility as described below.

IMPDH is involved in the de novo synthesis of guanosine nucleotides. IMPDH catalyzes the irreversible AND-dependent oxidation of inosine-5'-monophosphate ("IMP") to xanthosine-5'-monophosphate ("XMP"), Jackson et al., *Nature* 256:331–333 (1975).

IMPDH is ubiquitous in eukaryotes, bacteria and protozoa. The prokaryotic forms share 30–40% sequence identity with the human enzyme.

Two distinct cDNA's encoding IMPDH have been identified and isolated.

These transcripts are labeled type I and type II and are of identical size (514 amino acids). Collart et al., *J. Biol. Chem.* 263:15769–15772 (1988); Natsumeda et al., *J. Biol. Chem.* 265:5292–5295 (1990); and U.S. Pat. No. 5,665,583 to Collart et al. These isoforms share 84% sequence identity. IMPDH type I and type II form tetramers in solution, the enzymatically active unit.

B and T-lymphocytes depend on the de novo, rather than salvage pathway, to generate sufficient levels of nucleotides necessary to initiate a proliferative response to mitogen or antigen. Due to the B and T cell's unique reliance on the de novo pathway, IMPDH is an attractive target for selectively inhibiting the immune system without also inhibiting the proliferation of other cells.

Immunosuppression has been achieved by inhibiting a variety of enzymes. Examples include: phosphatase calcineurin (inhibited by cyclosporin and FK-506); dihydroorotate dehydrogenase (DHODase), an enzyme involved in the biosynthesis of pyrimidines (inhibited by leflunomide and brequinar); the kinase FRAP (inhibited by rapamycin); and the heat shock protein hsp70 (inhibited by deoxyspergualin).

Inhibitors of IMPDH have also been described in the art. WO 97/40028 and U.S. Pat. No. 5,807,876 describe a class of urea derivatives that possess a common urea backbone. A large number of compounds are described in WO 97/40028 and U.S. Pat. No. 5,807,876, but several of the compounds suffer from drawbacks such as inferior solubility. A recent publication, WO 98/40381, describes a series of heterocyclic substituted anilines as inhibitors of IMPDH.

U.S. Pat. No. 5,380,879 and 5,444,072 and PCT publications WO 94/01105 and WO 94/12184 describe mycophenolic acid ("MPA") and some of its derivatives as potent, uncompetitive, reversible inhibitors of human IMPDH type I and type II. MPA has been demonstrated to block the response of B and T-cells to mitogen or antigen. Immunosuppressants, such as MPA and derivatives of MPA, are useful drugs in the treatment of transplant rejection and autoimmune disorders, psoriasis, inflammatory diseases, including, rheumatoid arthritis, tumors and for the treatment of allograft rejection. These are described in U.S. Pat. Nos. 4,686234, 4,725622, 4,727,069, 4,753,935, 4,786,637, 4,808,592, 4,861,776, 4,868,153, 4,948,793, 4,952,579, 4,959,387, 4,992,467; 5.247,083; and U.S. patent application Ser. No. 07/927,260, filed Aug. 7, 1992. MPA does display undesirable pharmacological properties, such as gastrointestinal toxicity and poor bioavailability.

Tiazofurin, ribavirin and mizoribine also inhibit IMPDH. These nucleoside analogs are competitive inhibitors of IMPDH, however these agents inhibit other AND dependent enzymes. This low level of selectivity for IMPDH limits the therapeutic application of tiazofurin, ribavirin and mizoribine. Thus, new agents which have improved selectivity for IMPDH would represent a significant improvement over the nucleoside analogs.

Mycophenolate mofetil, sold under the trade name CELLCEPT, is a prodrug which liberates MPA in vivo. It is approved for use in preventing acute renal allograft rejection following kidney transplantation. The side effect profile limits the therapeutic potential of this drug. MPA is rapidly metabolized to the inactive glucuronide in vivo. In humans, the blood levels of glucuronide exceed that of MPA. The glucuronide undergoes enterohepatic recycling causing accumulation of MPA in the bile and subsequently in the gastrointestinal tract. This together with the production of the inactive glucuronide effectively lowers the drug's in vivo potency, while increasing its undesirable gastrointestinal side effects.

Unlike type I, type II mRNA is preferentially upregulated in human leukemic cell lines K562 and HL-60. Weber, J. Biol. Chem. 266: 506–509 (1991). In addition, cells from human ovarian tumors and leukemic cells from patients with chronic granulocytic, lymphocytic and acute myeloid leukemias also display an up regulation type II mRNA. This disproportionate increase in IMPDH activity in malignant cells may be addressed through the use of an appropriate IMPDH inhibitor. IMPDH has also been shown to play a role in the proliferation of smooth muscle cells, indicating that inhibitors of IMPDH may be useful in preventing restenosis or other hyperproliferative vascular diseases.

IMPDH has been shown to play a role in viral replication in some viral cell lines. Carr, *J. Biol. Chem.* 268:27286–27290 (1993). The IMPDH inhibitor VX-497, is currently being evaluated for the treatment of hepatitis C virus in humans. Ribavirin has also been used in the treatment of hepatitis C and B viruses and when used in combination with interferon an enhancement in activity was observed. The IMPDH inhibitor ribavirin is limited by its lack of a sustained response in monotherapy and broad cellular toxicity.

There remains a need for potent selective inhibitors of IMPDH with improved pharmacological properties, physical properties and fewer side effects. Such inhibitors would have therapeutic potential as immunosuppressants, anti-cancer agents, anti-vascular hyperproliferative agents, anti-inflammatory agents, antifungal agents, antipsoriatic and anti-viral agents. The compounds of the present invention differ from those taught by the prior art and are effective inhibitors of IMPDH.

SUMMARY OF THE INVENTION

The present invention provides compounds of the following formula I, stereoisomeric forms thereof, tautomeric forms thereof, pharmaceutically acceptable salt forms thereof, or prodrug forms thereof, for use as inhibitors of IMPDH enzyme:

(I)

wherein:
Z is a monocyclic or bicyclic ring system optionally containing up to 4 heteroatoms selected from N, O, and S, and wherein a $CH_2$ adjacent to any of the said N, O or S heteroatoms is optionally substituted with oxo (=O), and wherein Z is optionally substituted with 0–5 substituents chosen from $R^1$, $R^2$, $R^3$ or $R^4$;

$R^1$ and $R^2$ are each independently selected from the group consisting of H, F, Cl, Br, I, $NO_2$, $CF_3$, CN, $OCF_3$, OH, $C_1-C_4$alkoxy-, $C_1-C_4$alkylcarbonyl-, $C_1-C_6$ alkyl, hydroxy $C_1-C_4$ alkyl-, $C_3-C_6$ alkenyl, $C_3-C_6$ alkynyl, $C_3-C_{10}$ cycloalkyl($C_0-C_4$alkyl)-, $H_2N(C_0-C_4)$alkyl-, $R^6HN(C_0-C_4)$alkyl-, $R^6R^7N(C_0-C_4)$alkyl-, $R^7S(C_0-C_4)$alkyl-, $R^7S(O)(C_0-C_4)$alkyl-, $R^7SO_2(C_0-C_4)$alkyl-, $R^6R^7NSO_2(C_0-C_4)$alkyl-, $HSO_3$, $HO_2C(C_0-C_4)$alkyl-, $R^6O_2C(C_0-C_4)$alkyl-, and $R^6R^7NCO(C_0-C_4)$alkyl-, or Alternatively, $R^1$ and $R^2$, when on adjacent carbon atoms, and when taken together are methylenedioxy or ethylenedioxy;

$R^3$ is a 5- or 6-membered heterocyclic ring system containing up to 4 heteroatoms selected from N, O, and S, said heterocyclic ring system being optionally substituted with 0–3 $R^5$, wherein when Rs is hydroxy the heterocycle may undergo tautomerization to an oxo species or may exist as an equilibrium mixture of both tautomers;

$R^4$ is selected from F, Cl, Br, I, $NO_2$, $CF_3$, CN, $C_1-C_4$alkoxy-, OH, oxo, $CF_3O$, haloalkyloxy, $C_0-C_4$ alkylhydroxy, $C_1-C_4$ alkyl-, $C_1-C_4$ alkylcarbonyl-, $C_0-C_4$ alkylOCOR$^6$, $C_0-C_4$ alkylOC(=O)OR$^6$, $C_0-C_4$ alkylOC(=O)NR$^6$R$^7$, $NH_2$, NHR$^6$, $C_0-C_4$ alkylNR$^6$, $C_0-C_4$ alkylNR$^7$C(=O)OR$^6$, $C_0-C_4$ alkylNR$^6$SO$_2$NR$^6$R$^7$, $C_0-C_4$ alkylNR$^7$SO$_2$R$^6$, $C_0-C_4$ alkylSR$^6$, $C_0-C_4$ alkylS(O)R$^6$, $C_0-C_4$ alkylSO$_2$R$^6$, $SO_3R^7$, $C_0-C_4$ alkylSO$_2$NR$^6$R$^7$, $C_0-C_4$alkyl SO$_2$NR$^7$CO(CR$^9$R$^{10}$)$_{0-3}$R$^6$, $C_0-C_4$ alkylCO$_2$H, $C_0-C_4$ alkylCO$_2$R$^6$, $C_0-C_4$ alkylCONR$^6$R$^7$, and $C_0-C_4$alkylCONR$^7$SO$_2$(CR$^9$R$^{10}$)$_{0-3}$R$^6$;

$R^5$ is selected from the group consisting of H, $C_1-C_4$ alkyl, $C_3-C_7$ cycloalkyl, F, Cl, Br, I, $NO_2$, CN, $CF_3$, $OCF_3$, OH, oxo, $C_1-C_4$alkoxy-, hydroxy$C_1-C_4$ alkyl-, $C_1-C_4$ alkylcarbonyl-, $CO_2H$, $CO_2R^6$, CONR$^6$R$^7$, NHR$^6$, and NR$^6$R$^7$;

$R^6$ is selected from the group consisting of H, $C_1-C_8$ alkyl, $C_3-C_6$ alkenyl, $C_3-C_6$ alkynyl, $C_3-C_{10}$ cycloalkyl($C_0-C_4$ alkyl)-, aryl($C_0-C_4$ alkyl)-, and heterocyclic ($C_0-C_4$ alkyl)-, wherein said aryl or heterocyclic groups are substituted with 0–2 substituents independently selected from the group consisting of $C_1-C_4$ alkyl, $C_1-C_4$ alkoxy, hydroxy $C_0-C_4$ alkyl, oxo, F, Cl, Br, $CF_3$, $NO_2$, CN, $OCF_3$, $NH_2$, NHR$^7$, NR$^7$R$^8$, SR$^7$, S(O)R$^7$, $SO_2R^7$, $SO_2NR^7R^8$, $CO_2H$, $CO_2R^7$, and CONR$^7R^8$;

$R^7$ and $R^8$ are each independently selected from the group consisting of H, $C_1-C_8$ alkyl, $C_3-C_6$ alkenyl, $C_3-C$, alkynyl, $C_3-C_{10}$ cycloalkyl($C_0-C_4$ alkyl)-, $C_1-C_6$ alkylcarbonyl, $C_3-C_7$ cycloalkyl($C_0-C_5$ alkyl) carbonyl, $C_1-C_6$ alkoxycarbonyl, $C_3-C_7$ cycloalkyl ($C_0-C_5$ alkoxy)carbonyl, aryl($C_1-C_5$ alkoxy)carbonyl, arylsulfonyl, aryl($C_0-C_4$ alkyl)-, heterocyclic($C_1-C_5$ alkoxy)carbonyl, heterocyclic sulfonyl and heterocyclic ($C_0-C_4$ alkyl)-, wherein said aryl or heterocyclic groups are substituted with 0–2 substituents independently selected from the group consisting of $C_1-C_4$ alkyl, $C_1-C_4$ alkoxy, F, Cl, Br, $CF_3$, CN, and $NO_2$;

alternatively, $R^6$ and $R^7$, or $R^6$ and $R^8$, or $R^7$ and $R^8$, when both substituents are on the same nitrogen atom [as in (—NR$^6R^7$) or (—NR$^7R^8$)], can be taken together with the nitrogen atom to which they are attached to form a heterocycle selected from the group consisting of 1-aziridinyl, 1-azetidinyl, 1-piperidinyl, 1-morpholinyl, 1-pyrrolidinyl, thiamorpholinyl, thiazolidinyl, and 1-piperazinyi, said heterocycle being optionally substituted with 0–3 groups selected from the group consisting of oxo, $C_1-C_6$ alkyl, $C_3-C_7$ cycloalkyl($C_0-C_4$ alkyl)-, $C_1-C_6$ alkylcarbonyl, $C_3-C_7$ cycloal($C_0-C_5$ alkyl)carbonyl, $C_1-C_6$ alkoxycarbonyl, $C_3-C_7$ cycloalkyl($C_0-C_5$ alkoxy)carbonyl, aryl($C_0-C_5$ alkyl), heterocyclic($C_0-C_5$ alkyl), aryl($C_1-C_5$ alkoxy) carbonyl, heterocyclic($C_1-C_5$ alkoxy)carbonyl, $C_1-C_6$ alkylsulfonyl, arylsulfonyl, and heterocyclicsulfonyl, wherein said aryl or heterocyclic groups are substituted with 0–2 substituents independently selected from the group consisting of $C_1-C_4$ alkyl, $C_1-C_4$ alkoxy, F, Cl, Br, $CF_3$, CN, and $NO_2$;

J is selected from the group consisting of —NR$^7$— and —(=O)—;

K is selected from the group consisting of —NR$^7$—, —C(=O)—, and —CHR$^9$—;

L is selected from the group consisting of a single bond, —C(=O), —CR$^{10}R^{11}$—, —C(=O)CR$^{10}R^{11}$—, —CR$^{10}R^{11}C(=O)$—, —CR$^{10}R^{11}C(=O)$—, —HR$^{15}$C—CHR$^{16}$—, and —R $^{15}$C=CR$^{16}$;

$R^9$ is selected from the group consisting of H, $C_1-C_8$ alkyl, $C_3-C_6$ alkenyl, $C_3-C_{10}$ cycloalkyl($C_0-C_4$ alkyl)-, aryl($C_0-C_4$ alkyl)-, and heterocyclic($C_0-C_4$ alkyl)-, wherein said aryl or heterocyclic groups are substituted with 0–2 substituents dependently selected from the group consisting of $C_1-C_4$ alkyl, $C_1-C_4$ alkoxy, F, Cl, Br, $CF_3$, and $NO_2$;

$R^{10}$ is selected from the group consisting of H, F, Cl, Br, $C_1-C_6$ alkoxy, $C_1-C_8$ alkyl, $C_3-C_6$ alkenyl, $C_3-C_{10}$ cycloalkyl($C_0-C_4$ alkyl)-, aryl($C_0-C_4$ alkyl)-, and terocyclic($C_0-C_4$ alkyl)-, wherein said aryl or heterocyclic groups are substituted with 0–2 substituents independently selected from the group consisting of $C_1-C_4$ alkyl, $C_1-C_4$ alkoxy, F, Cl, Br, $CF_3$, CN, and $NO_2$;

$R^{11}$ is selected from the group consisting of H, F, Cl, Br, OMe, $C_1-C_8$ alkyl, $C_3-C_6$ alkenyl, $C_3-C_{10}$ cycloalkyl ($C_0-C_4$ alkyl)-, aryl($C_0-C_4$ alkyl)-, and heterocyclic ($C_0$–$C_4$ alkyl)-, wherein said aryl or heterocyclic groups are substituted with 0–2 substituents independently selected from the group consisting of $C_1$–$C_4$ alkyl, $C_1$–$C_4$ alkoxy, F, Cl, Br, $CF_3$, CN, and $NO_2$;

alternatively, $R^{10}$ and $R^{11}$, when on the same carbon atom [as in (—$CR^{10}R^{11}$—)], can be taken together with the carbon atoms to which they are attached to form a 3–7 membered carbocyclic or 3–7 membered heterocyclic non-aromatic ring system, said carbocyclic or heterocyclic ring being optionally substituted with 0–2 substituents independently selected from the group consisting of $C_1$–$C_4$ alkyl, $C_1$–$C_4$ alkoxy, hydroxy $C_0$–$C_4$ alkyl, oxo, F, Cl, Br, $CF_3$, and $NO_2$;

X is selected from the group consisting of $OR^{12}$, $NR^{12}R^{13}$, $C_1$–$C_8$ alkyl, $C_3$–$C_6$ alkenyl, $C_3$–$C_{10}$ cycloalkyl($C_0$–$C_4$ alkyl)-, $C_6$–$C_{10}$ aryl($C_0$–$C_4$ alkyl)-, and heterocyclic($C_0$–$C_4$ alkyl)-, wherein said aryl or heterocyclic groups are substituted with 0–3 substituents independently selected from $R^{14}$, with the proviso that when L is a single bond, X cannot be $NR^{12}R^{13}$;

$R^{12}$ is selected from the group consisting of H, $C_1$–$C_8$ alkyl, $C_3$–$C_6$ alkenyl, $C_3$–$C_{10}$ cycloalkyl($C_0$–$C_4$ alkyl)-, monocyclic or bicyclic aryl($C_0$–$C_4$ alkyl)-, and monocyclic or bicyclic 5–10 membered heterocyclic ($C_0$–$C_4$ alkyl)-, and —$CZ^1Z^2Z^3$, wherein said aryl or heterocyclic groups are substituted with 0–3 substituents independently selected from $R^{14}$;

$Z^1$ is selected from the group consisting of $C_1$–$C_8$ alkyl, $C_2$–$C_6$ alkenyl, $C_2$–$C_6$ alkynyl, $C_1$–$C_6$ hydroxyalkyl, $C_1$–$C_4$ alkoxy $C_1$–$C_4$ alkyl, aryl($C_0$–$C_4$ alkyl)-, and 4–10 membered heterocyclic ($C_0$–$C_4$ alkyl)-, wherein said aryl or heterocyclic groups are substituted with 0–3 substituents independently selected from $R^{14}$;

$Z^2$ is selected from the group consisting of $C_1$–$C_8$ alkyl, $C_2$–$C_6$ alkenyl, $C_2$–$C_6$ alkynyl, $C_1$–$C_6$ hydroxyalkyl, $C_1$–$C_4$ alkoxy $C_1$–$C_4$ alkyl, $C_1$–$C_6$ $NR^{17}R^{18}$, aryl ($C_0$–$C_4$ alkyl)-, and 4–10 membered heterocyclic ($C_0$–$C_4$ alkyl)-, wherein said aryl or heterocyclic groups are substituted with 0–3 substituents independently selected from $R^{14}$;

$Z^3$ is selected from the group consisting of $C_1$–$C_8$ alkyl, $R^{14}(C_2$–$C_4$ alkyl)-, $C_2$–$C_6$ alkenyl, $C_2$–$C_6$ alkynyl, $C_1$–$C_6$ hydroxyalkyl, $C_1$–$C_4$ alkoxy $C_1$–$C_4$ alkyl, aryl ($C_0$–$C_4$ alkyl)-, 4–10 membered heterocyclic ($C_0$–$C_4$ alkyl)-, $R^{17}O$=$C(C_0$–$C_4$ alkyl)-, $R^{17}OO$=$C(C_0$–$C_4$ alkyl)-, and $R^{17}R^{18}$ NO=$C(C_0$–$C_4$ alkyl)-, wherein said aryl or heterocyclic groups are substituted with 0–3 substituents independently selected from $R^{14}$;

alternatively, $Z^1$ and $Z^2$, when on the same carbon atom [as in (—$CZ^1 Z^2$—)], can be taken together with the carbon atoms to which they are attached to form a 3–7 membered carbocyclic or 3–7 membered heterocyclic non-aromatic ring system, said carbocyclic or heterocyclic ring being optionally substituted with 0–2 substituents independently selected from $R^{14}$.

$R^{13}$ is selected from the group consisting of H, $C_1$–$C_8$ alkyl, $C_3$–$C_6$ alkenyl, $C_3$–$C_{10}$ cycloalkyl($C_0$–$C_4$ alkyl)-, $C_1$–$C_6$ alkylcarbonyl, $C_1$–$C_6$ alkylsulfonyl, $C_3$–$C_7$ cycloalkyl($C_0$–$C_5$ alkyl)carbonyl, $C_1$–$C_6$ alkoxycarbonyl, $C_3$–$C_7$ cycloalkyl($C_0$–$C_5$ alkoxy) carbonyl, aryl($C_0$–$C_4$ alkyl)-, aryl($C_1$–$C_5$ alkoxy) carbonyl , arylsulfonyl, heterocyclic($C_0$–$C_4$ alkyl), heterocyclic($C_1$–$C_5$ alkoxy)carbonyl, and heterocyclicsulfonyl, wherein said aryl or heterocyclic groups are substituted with 0–2 substituents independently selected from the group consisting of $C_1$–$C_4$ alkyl, $C_1$–$C_4$ alkoxy, F, Cl, Br, $CF_3$, CN, and $NO_2$;

alternatively, $R^{12}$ and $R^{13}$, when both are on the same nitrogen atom [as in (—$NR^{12}R^{13}$)] can be taken together with the nitrogen atom to which they are attached to form a heterocycle selected from 1-aziridinyl, 1-azetidinyl, 1-piperidinyl, 1-morpholinyl, 1-pyrrolidinyl, thiamorpholinyl, thiazolidinyl, and 1-piperazinyl, said heterocycle being optionally substituted with 0–3 groups independently selected from oxo, $C_1$–$C_6$ alkyl, $C_3$–$C_7$ cycloalkyl($C_0$–$C_4$ alkyl)-, $C_1$–$C_6$ alkylcarbonyl, $C_3$–$C_7$ cycloalkyl($C_0$–$C_5$ alkyl)carbonyl, $C_1$–$C_6$ alkoxycarbonyl, $C_3$–$C_7$ cycloalkyl($C_0$–$C_5$ alkoxy) carbonyl, aryl($C_0$–$C_5$ alkyl), heterocyclic($C_0$–$C_5$ alkyl), aryl($C_1$–$C_5$ alkoxy)carbonyl, heterocyclic ($C_1$–$C_5$ alkoxy)carbonyl, $C_1$–$C_6$ alkylsulfonyl arylsulfonyl and heterocyclicsulfonyl, wherein said aryl or heterocyclic groups are substituted with 0–2 substituents independently selected from the group consisting of $CH_3$-, alkoxy, F, Cl, Br, $CF_3$, CN, and $NO_2$;

$R^{14}$ is selected from the group consisting of H, $C_1$–$C_{10}$ alkyl, $NO_2$, $CF_3$, CN, F, Cl, Br, $C_1$–$C_{10}$ alkylcarbonyl, haloalkyl, haloalkoxy, OH, $NR^6R^7(C_0$–$C_4$ alkyl)-, $R^6$ C(=O)O($C_0$–$C_4$ alkyl)-, $R^6OC(=O)O$ ($C_0$–$C_4$ alkyl)-, $R^6O$ ($C_0$–$C_4$ alkyl), $R^6R^7$ NC(=O) O($C_0$–$C_4$ alkyl)-, $R^6R^7$ NC(=O) ($C_0[\N]C_4$ alkyl)-, $R^6O(CR^{10}R^{11})_{2-6}$ $R^6NC(=O)$ ($C_0$–$C_4$ alkyl)-, $R^6R^7N(CR^{10}R^{11})_{2-6}R^6NC$ (=O) ($C_0$–$C_4$ alkyl)-, $R^6O_2C(CH_2)_{1-4}O(C_0$–$C_4$ alkyl)-, $R^6OOC(C_1$–$C_4$ alkoxy), —$R^6OOC(C_0$–$C_4$ alkyl)-, $R^6C(=O)(C_0$–$C_4$ alkyl)-, $R^6C(=O)NR^7$ ($C_0$–$C_4$ alkyl)-, $R^6OC(=O)NR^7(C_0$–$C_4$ alkyl)-, $R^6OC$ (=NCN)$NR^7(C_0$–$C_4$ alkyl)-, $R^6R^7NC(=O)NR^8$ ($C_0$–$C_4$ alkyl)-, $R^6OC(=NC)$ $NR^7(C_0$–$C_4$ alkyl)-, $R^6(CR^{10}R^{11})_{1-4}$ $NR^7C$=O—, $R^6O(CR^{10}R^{11})_{1-4}$ O=$CR^7N$—, $NR^6R^7(CR^{10}R^{11})_{1-4}$ C=O $R^7N$—,$R^6O$ $(CR^{10}R^{11})_{2-4}R^7N$—, $R^6O_2C(CR^{10}R^{11})_{1-4}R^7N$, $R^6R^7N$ $(CR^{10}R^{11})_{2-4}R^7N$—, $R^6R^7NC(=NCN)NR^7(C_0$–$C_4$ alkyl)-, $R^6R^7NC(=C(H)(NO_2))NR^7(C_0$–$C_4$ alkyl)-, $R^7R^8N$ C(=$NR^7$) $NR^7(C_0$–$C_4$ alkyl)-, $R^6R^1N$ $SO_2NR^8$ ($C_0$–$C_4$ alkyl)-, $R^6SO_2NR^7(C_0$–$C_4$ alkyl)-, $R^6R^7N$ ($C_1$–$C_4$) CO—, $R^6R^7N(C_2$–$C_6$ alkyl)O—, $R^6CO$ $(CR^{10}R^{11})_{0-2}$ $R^7N(O_2)S(C_0$–$C_4$ alkyl), $R^6(O_2)S$ $R^7$ NC(=O) ($C_0$–$C_4$ alkyl)-, $R^6S(C_0$–$C_4$ alkyl)-, $R^6S$ (=O) ($C_0$–$C_4$ alkyl)-, $R^6SO_2(C_0$–$C_4$ alkyl)-, $SO_2N^6R^7$, $SiMe_3$, $R^6R^7N(C_2$–$C_4$ alkyl)-, $R^6R^7N(C_2$–$C_4$ alkoxy)-, $HSO_3$, HONH—, $R^6ONH$—, $R^8R^7NNR^6$—, HO(COR^6)N—, HO($R^6O_2C)N$, $C_2$–$C_6$ alkenyl, $C_3$–$C_{10}$ cycloalkyl, $C_3$–$C_{10}$ cycloalkylmethyl, aryl ($C_0$–$C_4$alkyl)-, heteroaryl($C_0$–$C_4$alkyl)-, aryl ($C_0$–$C_4$alkyl)O—, and heteroaryl($C_0$–$C_4$alkyl)O—, wherein said aryl groups are substituted with 0–2 substituents independently selected from a group consisting of $C_1$–$C_4$ alkyl, $C_1$–$C_4$ alkoxy, F, Cl, Br, $CF_3$, and $NO_2$;

$R^{15}$ is selected from the group consisting of H, halo, cyano, $C_1$–$C_8$ alkyl, $C_3$–$C_6$ alkenyl, and $C_3$–$C_{10}$ cycloalkyl($C_0$–$C_4$ alkyl)-, aryl($C_0$–$C_4$ alkyl)-, and heterocyclic($C_0$–$C_4$ alkyl)-, wherein said aryl or heterocyclic groups are substituted with 0–2 substituents independently selected from $R^{14}$;

$R^{16}$ is selected from the group consisting of H, halo, cyano, $C_1$–$C_8$ alkyl, $C_3$–$C_6$ alkenyl, $C_3$–$C_{10}$ cycloalkyl ($C_0$–$C_4$ alkyl)-, aryl($C_0$–$C_4$ alkyl)-, and heterocyclic ($C_0$–$C_4$ alkyl)-,
wherein said aryl or heterocyclic groups are substituted with 0–2 substituents independently selected from $R^{14}$;
alternatively, when $R^{15}$ and $R^{16}$ are on adjacent carbon atoms [as in —$HR^{15}C$—$CHR^{16}$—], or when $R^{15}$ and $R^{16}$ are oriented on the same side of the double bond [as in the following structure (III)

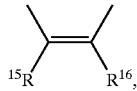

(III)]

$R^{15}$ and $R^{16}$ can be taken together with the carbon atoms to which they are attached to form a 3–7 membered carbocyclic aromatic or nonaromatic ring system, or a 3–7 membered heterocyclic aromatic or nonaromatic ring system, said carbocyclic or heterocyclic ring being optionally substituted with 0–2 substituents independently selected from the group consisting of $C_1$–$C_4$ alkyl, $C_1$–$C_4$ alkoxy, F, Cl, Br, $CF_3$, $NO_2$;

$R^{17}$ is selected from the group consisting of H, $C_1$–$C_8$ alkyl, $C_3$–$C_6$ alkenyl, $C_3$–$C_{10}$ cycloalkyl($C_0$–$C_4$ alkyl)-, $C_1$–$C_6$ alkylcarbonyl, $C_{1-C6}$ alkylsulfonyl, $C_3$–$C_7$ cycloalkyl($C_0$–$C_5$ alkyl)carbonyl, $C_1$–$C_6$ alkoxycarbonyl, $C_3$–$C_7$ cycloalkyl($C_0$–$C_5$ alkoxy)carbonyl, hydroxy($C_2$–$C_4$)alkyl-, $C_1$–$C_3$ alkoxy ($C_2$–$C_4$)alkyl-, ($C_0$–$C_4$ alkyl) ($C_0$–$C_4$ alkyl) amino ($C_2$–$C_4$)alkyl-, aryl($C_0$–$C_4$ alkyl)-, aryl($C_1$–$C_5$ alkoxy) carbonyl, arylsulfonyl, heterocyclic($C_0$–$C_4$ alkyl), heterocyclic($C_1$–$C_5$ alkoxy)carbonyl, and heterocyclicsulfonyl,
wherein said aryl or heterocyclic groups are substituted with 0–2 substituents independently selected from the group consisting of $C_1$–$C_4$ alkyl, $C_1$–$C_4$ alkoxy, $C_1$–$C_4$ alkoxy $C_1$–$C_4$ alkyl, oxo, F, Cl, Br, $CF_3$, CN, and $NO_2$;

$R^{18}$ is selected from the group consisting of H, $C_1$–$C_8$ alkyl, $C_3$–$C_6$ alkenyl, $C_3$–$C_{10}$ cycloalkyl($C_0$–$C_4$ alkyl)-, aryl($C_0$–$C_4$ alkyl)-, and heterocyclic($C_0$–$C_4$ alkyl),
wherein said aryl or heterocyclic groups are substituted with 0–2 substituents independently selected from the group consisting of $C_1$–$C_4$ alkyl, $C_1$–$C_4$ alkoxy, F, Cl, Br, $CF_3$, CN, and $NO_2$; and
alternatively, $R^{17}$ and $R^{18}$, when both are on the same nitrogen atom [as in (—$NR^{12}R^{13}$)] can be taken together with the nitrogen atom to which they are attached to form a heterocycle selected from 1-aziridinyl, 1-azetidinyl, 1-piperidinyl, 1-morpholinyl, 1-pyrrolidinyl, thiamorpholinyl, thiazolidinyl, and 1-piperazinyl,
said heterocycle being optionally substituted with 0–3 groups selected from oxo, $C_1$–$C_6$ alkyl, $C_3$–$C_7$ cycloalkyl($C_0$–$C_4$ alkyl)-, $C_1$–$C_6$ alkylcarbonyl, ($C_1$–$C_6$ alkylcarbonyl)($C_0$–$C_4$alkyl)amino-, $C_3$–$C_7$ cycloalkyl($C_0$–$C_5$ alkyl)carbonyl, $C_1$–$C_6$ alkoxycarbonyl, $C_3$–$C_7$ cycloalkyl($C_0$–$C_5$ alkoxy)carbonyl, aryl($C_0$–$C_5$ alkyl), heterocyclic($C_0$–$C_5$ alkyl), aryl($C_1$–$C_5$ alkoxy)carbonyl, heterocyclic ($C_1$–$C_5$ alkoxy)carbonyl, $C_1$–$C_6$ alkylsulfonyl arylsulfonyl and heterocyclicsulfonyl,
wherein said aryl or heterocyclic groups are substituted with 0–2 substituents independently selected from the group consisting of $CH_3$—, alkoxy, F, Cl, Br, $CF_3$, CN, and $NO_2$.

Compounds of formula I, their enantiomers, diastereomers, tautomers and pharmaceutically acceptable salts, prodrugs and solvates thereof, are novel.

The present invention also provides pharmaceutical compositions comprising the compounds of formula I and methods of treating IMPDH-associated disorders using the compounds of formula I.

The compounds of the present invention offer therapeutic advantages over known prior art compounds, and are useful in treating IMPDH-associated disorders. These advantages include increased solubility (which in turn increases overall therapeutic benefit) and reduction in negative side effects.

DETAILED DESCRIPTION OF THE INVENTION

As described above, the present invention encompasses compounds of the following formula I, stereoisomeric forms thereof, tautomeric forms thereof, pharmaceutically acceptable salt forms thereof, or prodrug forms thereof:

(I)

wherein:
Z is a monocyclic or bicyclic ring system optionally containing up to 4 heteroatoms selected from N, O, and S, and wherein a $CH_2$ adjacent to any of the said N, O or S heteroatoms is optionally substituted with oxo (=O), and wherein Z is optionally substituted with 0–5 substituents chosen from $R^1$, $R^2$, $R^3$ or $R^4$;

$R^1$ and $R^2$ are each independently selected from the group consisting of H, F, Cl, Br, I, $NO_2$, $CF_3$, CN, $OCF_3$, OH, $C_1$–$C_4$alkoxy-, $C_1$–$C_4$alkylcarbonyl-, $C_1$–$C_6$ alkyl, hydroxy $C_1$–$C_4$ alkyl-, $C_3$–$C_6$ alkenyl, $C_3$–$C_6$ alkynyl, $C_3$–$C_{10}$ cycloalkyl($C_0$–$C_4$alkyl)-, $H_2N(C_0$–$C_4$)alkyl-, $R^6HNC_0$–$C_4$)alkyl-, $R^6R^7N$($C_0$–$C_4$)alkyl-, $R^7S(C_0$–$C_4$)alkyl-, $R^7S(O)$ ($C_0$–$C_4$) alkyl-, $R^7SO_2(C_0$–$C_4$)alkyl-, $R^6R^7NSO_2(C_0$–$C_4$) alkyl-, $HSO_3$, $HO_2C(C_0$–$C_4$)alkyl-, $R^6O_2C(C_0$–$C_4$) alkyl-, and $R^6R^7NCO(C_0$–$C_4$)alkyl-, or Alternatively, $R^1$ and $R^2$, when on adjacent carbon atoms, and when taken together are methylenedioxy or ethylenedioxy;

$R^3$ is a 5- or 6-membered heterocyclic ring system containing up to 4 heteroatoms selected from N, O, and S, said heterocyclic ring system being optionally substituted with 0–3 $R^5$, wherein when $R^5$ is hydroxy the heterocycle may undergo tautomerization to an oxo species or may exist as an equilibrium mixture of both tautomers;

$R^4$ is selected from F, Cl, Br, I, $NO_2$, $CF_3$, CN, $C_1$–$C_4$alkoxy-, OH, oxo, $CF_3O$, haloalkyloxy, $C_0$–$C_4$ alkylhydroxy, $C_1$–C4 alkyl-, $C_1$–$C_4$ alkylcarbonyl-, $C_0$–$C_4$ alkylOCOR$^6$, $C_0$–$C_4$ alkylOC(=O)OR$^6$, $C_0$–$C_4$ alkylOC(=O)NR$^6R^7$, $NE_2$, $NHR^6$, $C_0$–$C_4$ alkylNR$^6R^7$, $C_0$–$C_4$ alkylNR$^7$C(=O)OR$^6$, $C_0$–$C_4$ alkylNR$^6SO_2NR^6R^7$, $C_0$–$C_4$ alkylNR$^7SO_2R^6$, $C_0$–$C_4$ alkylSR$^6$, $C_0$–$C_4$ alkylS(O)R$^6$, $C_0$–$C_4$ alkylSO$_2R^6$, $SO_3R^7$, $C_0$–$C_4$ alkylSO$_2NR^6R^7$, $C_0$–$C_4$alkyl $SO_2NR^7$ CO(CR$^9R^{10})_{0-3}R^6$, $C_0$–$C_4$ alkylCO$_2$H, $C_0$–$C_4$ alkylCO$_2R^6$, $C_0$–$C_4$ alkylCONR$^6R^7$, and $C_0$–$C_4$alkylCONR$^7SO_2$ (CR$^9R^{10})_{0-3}R^6$;

$R^5$ is selected from the group consisting of H, $C_1$–$C_4$ alkyl, $C_3$–$C_7$ cycloalkyl, F, Cl, Br, I, $NO_2$, CN, $CF_3$, $OCF_3$, OH, oxo, $C_1$–$C_4$alkoxy-, hydroxy$C_1$–$C_4$ alkyl-, $C_1$–$C_4$ alkylcarbonyl-, $CO_2H$, $CO_2R^6$, $CONR^6R^7$, $NHR^6$, and $NR^6R^7$;

$R^6$ is selected from the group consisting of H, $C_1$–$C_8$ alkyl, $C_3$–$C_6$ alkenyl, $C_3$–$C_6$ alkynyl, $C_3$–$C_{10}$ cycloalkyl($C_0$–$C_4$ alkyl)-, aryl($C_0$–$C_4$ alkyl)-, and heterocyclic ($C_0$–$C_4$ alkyl)-, wherein said aryl or heterocyclic groups are substituted with 0–2 substituents independently selected from the group consisting of $C_1$–$C_4$ alkyl, $C_1$–$C_4$ alkoxy, hydroxy $C_0$–$C_4$ alkyl, oxo, F, Cl, Br, $CF_3$, $NO_2$, CN, $OCF_3$, $NH_2$, $NHR^7$, $NR^7R^8$, $SR^7$, $S(O)R^7$, $SO_2R^7$, $SO_2NR^7R^8$, $CO_2H$, $CO_2R^7$, and $CONR^7R^8$;

$R^7$ and $R^8$ are each independently selected from the group consisting of H, $C_1$–$C_8$ alkyl, $C_3$–$C_6$ alkenyl, $C_3$–$C_6$ alkynyl, $C_3$–$C_{10}$ cycloalkyl($C_0$–$C_4$ alkyl)-, $C_1$–$C_6$ alkylcarbonyl, $C_3$–$C_7$ cycloalkyl($C_0$–$C_5$ alkyl)carbonyl, $C_1$–$C_6$ alkoxycarbonyl, $C_3$–$C_7$ cycloalkyl($C_0$–$C_5$ alkoxy)carbonyl, aryl($C_1$–$C_5$ alkoxy)carbonyl, arylsulfonyl, aryl($C_0$–$C_4$ alkyl)-, heterocyclic($C_1$–$C_5$ alkoxy)carbonyl, heterocyclic sulfonyl and heterocyclic ($C_0$–$C_4$ alkyl)-, wherein said aryl or heterocyclic groups are substituted with 0–2 substituents independently selected from the group consisting of $C_1$–$C_4$ alkyl, $C_1$–$C_4$ alkoxy, F, Cl, Br, $CF_3$, CN, and $NO_2$;

alternatively, $R^6$ and $R^7$, or $R^6$ and $R^8$, or $R^7$ and $R^8$, when both substituents are on the same nitrogen atom [as in (—$NR^6R^7$) or (—$NR^7R^8$)], can be taken together with the nitrogen atom to which they are attached to form a heterocycle selected from the group consisting of 1-aziridinyl, 1-azetidinyl, 1-piperidinyl, 1-morpholinyl, 1-pyrrolidinyl, thiamorpholinyl, thiazolidinyl, and 1-piperazinyl, said heterocycle being optionally substituted with 0–3 groups selected from the group consisting of oxo, $C_1$–$C_6$ alkyl, $C_3$–$C_7$ cycloalkyl($C_0$–$C_4$ alkyl)-, $C_1$–$C_6$ alkylcarbonyl, $C_3$–$C_7$ cycloalkyl($C_0$–$C_5$ alkyl)carbonyl, $C_1$–$C_6$ alkoxycarbonyl, $C_3$–$C_7$ cycloalkyl($C_0$–$C_5$ alkoxy)carbonyl, aryl($C_0$–$C_5$ alkyl), heterocyclic($C_0$–$C_5$ alkyl), aryl($C_1$–$C_5$ alkoxy)carbonyl, heterocyclic($C_1$–$C_5$ alkoxy)carbonyl, $C_1$–$C_6$ alkylsulfonyl, arylsulfonyl, and heterocyclicsulfonyl, wherein said aryl or heterocyclic groups are substituted with 0–2 substituents independently selected from the group consisting of $C_1$–$C_4$ alkyl, $C_1$–$C_4$ alkoxy, F, Cl, Br, $CF_3$, CN, and $NO_2$;

J is selected from the group consisting of —$NR^7$— and —C(=O)—;

K is selected from the group consisting of —$NR^7$—, —C(=O)—, and —$CHR^9$—;

L is selected from the group consisting of a single bond, —C(=O), —$CR^{10}R^{11}$—, —C(=O)$CR^{10}R^{11}$—, —$CR^{10}R^{11}$C(=O)—, —$CR^{10}R^{11}$C(=O)—, —$HR^{15}C$—$CHR^{16}$—, and —$R^{15}C$=$CR^{16}$;

$R^9$ is selected from the group consisting of H, $C_1$–$C_8$ alkyl, $C_3$–$C_6$ alkenyl, $C_3$–$C_{10}$ cycloalkyl($C_0$–$C_4$ alkyl)-, aryl($C_0$–$C_4$ alkyl)-, and heterocyclic($C_0$–$C_4$ alkyl)-, wherein said aryl or heterocyclic groups are substituted with 0–2 substituents independently selected from the group consisting of $C_1$–$C_4$ alkyl, $C_1$–$C_4$ alkoxy, F, Cl, Br, $CF_3$, and $NO_2$;

$R^{10}$ is selected from the group consisting of H, F, Cl, Br, $C_1$–$C_6$ alkoxy, $C_1$–$C_8$ alkyl, $C_3$–$C_6$ alkenyl, $C_3$–$C_{10}$ cycloalkyl($C_0$–$C_4$ alkyl)-, aryl($C_0$–$C_4$ alkyl)-, and heterocyclic($C_0$–$C_4$ alkyl)-, wherein said aryl or heterocyclic groups are substituted with 0–2 substituents independently selected from the group consisting of $C_1$–$C_4$ alkyl, $C_1$–$C_4$ alkoxy, F, Cl, Br, $CF_3$, CN, and $NO_2$;

$R^{11}$ is selected from the group consisting of H, F, Cl, Br, OMe, $C_1$–$C_8$ alkyl, $C_3$–$C_6$ alkenyl, $C_3$–$C_{10}$ cycloalkyl($C_0$–$C_4$ alkyl)-, aryl($C_0$–$C_4$ alkyl)-, and heterocyclic($C_0$–$C_4$ alkyl)-, wherein said aryl or heterocyclic groups are substituted with 0–2 substituents independently selected from the group consisting of $C_1$–$C_4$ alkyl, $C_1$–$C_4$ alkoxy, F, Cl, Br, $CF_3$, CN, and $NO_2$;

alternatively, $R^{10}$ and $R^{11}$, when on the same carbon atom [as in (—$CR^{10}R^{11}$—)], can be taken together with the carbon atoms to which they are attached to form a 3–7 membered carbocyclic or 3–7 membered heterocyclic non-aromatic ring system, said carbocyclic or heterocyclic ring being optionally substituted with 0–2 substituents independently selected from the group consisting of $C_1$–$C_4$ alkyl, $C_1$–$C_4$ alkoxy, hydroxy $C_0$–$C_4$ alkyl, oxo, F, Cl, Br, $CF_3$, and $NO_2$;

X is selected from the group consisting of $OR^{12}$, $NR^{12}R^{13}$, $C_1$–$C_8$ alkyl, $C_3$–$C_6$ alkenyl, $C_3$–$C_{10}$ cycloalkyl($C_0$–$C_4$ alkyl)-, $C_6$–$C_{10}$ aryl($C_0$–$C_4$ alkyl)-, and heterocyclic($C_0$–$C_4$ alkyl)-, wherein said aryl or heterocyclic groups are substituted with 0–3 substituents independently selected from $R^{14}$, with the proviso that when L is a single bond, X cannot be $NR^{12}R^{13}$;

$R^{12}$ is selected from the group consisting of H, $C_1$–$C_8$ alkyl, $C_3$–$C_6$ alkenyl, $C_3$–$C_{10}$ cycloalkyl($C_0$–$C_4$ alkyl)-, monocyclic or bicyclic aryl($C_0$–$C_4$ alkyl)-, and monocyclic or bicyclic 5–10 membered heterocyclic($C_0$–$C_4$ alkyl)-, and —$CZ^1Z^2Z^3$, wherein said aryl or heterocyclic groups are substituted with 0–3 substituents independently selected from $R^{14}$;

$Z^1$ is selected from the group consisting of $C_1$–$C_8$ alkyl, $C_2$–$C_6$ alkenyl, $C_2$–$C_6$ alkynyl, $C_1$–$C_6$ hydroxyalkyl, $C_1$–$C_4$ alkoxy $C_1$–$C_4$ alkyl, aryl($C_0$–$C_4$ alkyl)-, and 4–10 membered heterocyclic ($C_0$–$C_4$ alkyl)-, wherein said aryl or heterocyclic groups are substituted with 0–3 substituents independently selected from $R^{14}$;

$Z^2$ is selected from the group consisting of $C_1$–$C_8$ alkyl, $C_2$–$C_6$ alkenyl, $C_2$–$C_6$ alkynyl, $C_1$–$C_6$ hydroxyalkyl, $C_1$–$C_4$ alkoxy $C_1$–$C_4$ alkyl, $C_1$–$C_6$ alkyl), aryl($C_0$–$C_4$ alkyl)-, and 4–10 membered heterocyclic ($C_0$–C, alkyl)-, wherein said aryl or heterocyclic groups are substituted with 0–3 substituents independently selected from $R^{14}$;

$Z^3$ is selected from the group consisting of $C_1$–$C_8$ alkyl, $R^{14}(C_2$–$C_4$ alkyl)-, $C_2$–$C_6$ alkenyl, $C_2$–$C_6$ alkynyl, $C_1$–$C_6$ hydroxyalkyl, $C_1$–$C_4$ alkoxy $C_{12}$–$C_4$ alkyl, aryl ($C_0$–$C_4$ alkyl)-, 4–10 membered heterocyclic ($C_0$–$C_4$ alkyl)-, $R^{17}O$=$C(C_0$–$C_4$ alkyl)-, $R^{17}OO$=$C(C_0$–$C_4$ alkyl)-, and $R^{17}R^{18}NO$=$C(C_0$–$C_4$ alkyl)-, wherein said aryl or heterocyclic groups are substituted with 0–3 substituents independently selected from $R^{14}$;

alternatively, $Z^1$ and $Z^2$, when on the same carbon atom [as in (—$CZ^1Z^2$—)], can be taken together with the carbon atoms to which they are attached to form a 3–7 membered carbocyclic or 3–7 membered heterocyclic non-aromatic ring system, said carbocyclic or heterocyclic ring being optionally substituted with 0–2 substituents independently selected from $R^{14}$.

$R^{13}$ is selected from the group consisting of H, $C_1$–$C_8$ alkyl, $C_3$–$C_6$ alkenyl, $C_3$–$C_{10}$ cycloalkyl($C_0$–$C_4$ alkyl)-, $C_1$–$C_6$ alkylcarbonyl, $C_1$–$C_6$ alkylsulfonyl, $C_3$–$C_7$ cycloalkyl($C_0$–$C_5$ alkyl)carbonyl, $C_1$–$C_6$ alkoxycarbonyl, $C_3$–$C_7$ cycloalkyl($C_0$–$C_5$ alkoxy)carbonyl, aryl($C_0$–$C_4$ alkyl)-, aryl($C_1$–$C_5$ alkoxy)carbonyl, arylsulfonyl, heterocyclic($C_0$–$C_4$ alkyl), heterocyclic($C_1$–$C_5$ alkoxy)carbonyl, and heterocyclicsulfonyl, wherein said aryl or heterocyclic groups are substituted with 0–2 substituents independently selected from the group consisting of $C_1$–$C_4$ alkyl, $C_1$–$C_4$ alkoxy, F, Cl, Br, $CF_3$, CN, and $NO_2$;

alternatively, $R^{12}$ and $R^{13}$, when both are on the same nitrogen atom [as in (—$NR^{12}R^{13}$)] can be taken together with the nitrogen atom to which they are attached to form a heterocycle selected from 1-aziridinyl, 1-azetidinyl, 1-piperidinyl, 1-morpholinyl, 1-pyrrolidinyl, thiamorpholinyl, thiazolidinyl, and 1-piperazinyl, said heterocycle being optionally substituted with 0–3 groups independently selected from oxo, $C_1$–$C_6$ alkyl, $C_3$–$C_7$ cycloalkyl($C_0$–$C_4$ alkyl)-, $C_1$–$C_6$ alkylcarbonyl, $C_3$–$C_7$ cycloalkyl($C_0$–$C_5$ alkyl)carbonyl, $C_1$–$C_6$ alkoxycarbonyl, $C_3$–$C_7$ cycloalkyl($C_0$–$C_5$ alkoxy)carbonyl, aryl($C_0$–$C_5$ alkyl), heterocyclic($C_0$–$C_5$ alkyl), aryl($C_1$–$C_5$ alkoxy)carbonyl, heterocyclic($C_1$–$C_5$ alkoxy)carbonyl, $C_1$–$C_6$ alkylsulfonyl arylsulfonyl and heterocyclicsulfonyl, wherein said aryl or heterocyclic groups are substituted with 0–2 substituents independently selected from the group consisting of $CH_3$—, alkoxy, F, Cl, Br, $CF_3$, CN, and $NO_2$;

$R^{14}$ is selected from the group consisting of H, $C_1$–$C_{10}$ alkyl, $NO_2$, $CF_3$, CN, F, Cl, Br, $C_1$–$C_{10}$ alkylcarbonyl, haloalkyl, haloalkoxy, OH, $NR^6R^7$ ($C_0$–$C_4$ alkyl)-, $R^6$ C(=O)O($C_0$–$C_4$ alkyl)-, $R^6$OC(=O)O ($C_0$–$C_4$ alkyl)-, $R^6$O($C_0$–$C_4$ alkyl), $R^6R^7$ NC(=O) O($C_0$–$C_4$ alkyl)-, $R^6R^7$ NC(=O) ($C_0$–$C_4$ alkyl)-, $R^6$O($CR^{10}OR^{11}$)$_{2-6}R^6$NC(=O) ($C_0$–$C_4$ alkyl)-, $R^6R^7$N($CR^{10}R^{11}$)$_{2-6}R^6$NC(=O) ($C_0$–$C_4$ alkyl)-, $R^6O_2C(CH_2)_{1-4}$O($C_0$–$C_4$ alkyl)-, $R^6$OOC ($C_1$–$C_4$ alkoxy), —$R^6$OOC($C_0$–$C_4$ alkyl)-, $R^6$C(=O)($C_0$–$C_4$ alkyl)-, $R^6$C(=O)$NR^7$($C_0$–$C_4$ alkyl)-, $R^6$OC(=O)$NR^7$($C_0$–$C_4$ alkyl)-, $R^6$OC(=NCN)$NR^7$ ($C_0$–$C_4$ alkyl)-, $R^6R^7$NC(=O)$NR^8$($C_0$–$C_4$ alkyl)-, $R^6$OC(=NC) $NR^7$($C_0$–$C_4$ alkyl)-, $R^6(CR^{10}R^{11})_{1-4}$ $NR^7$C=O—, $R^6$O($CR^{10}R^{11}$)$_{1-4}$O=$CR^7$N—, $NR^6R^7$($CR^{10}R^{11}$)$_{1-4}$ C=O $R^7$N—, $R^6$O ($CR^{10}R^{11}$)$_{2-4}R^7$N—, $R^6O_2C(CR^{10}R^{11})_{1-4}R^7$N, $R^6R^7$N ($CR^{10}R^{11}$)$_{2-4}R^7$N—, $R^6R^7$NC(=NCN)$NR^7$($C_0$–$C_4$ alkyl)-, $R^6R^7$NC(=C(H)($NO_2$))$NR^7$($C_0$–$C_4$ alkyl)-, $R^7R^8$N C(=$NR^7$) $NR^7$($C_0$–$C_4$ alkyl)-, $R^6R^7$N $SO_2NR^8$($C_0$–$C_4$ alkyl)-, $R^6SO_2NR^7$($C_0$–$C_4$ alkyl)-, $R^6R^7$N($C_1$–$C_4$) CO—, $R^6R^7$N($C_2$–$C_6$ alkyl)O—, $R^6CO(CR^{10}R^{11})_{0-2}$ $R^7N(O_2)S(C_0$–$C_4$ alkyl), $R^6(O_2)S$ $R^7$ NC(=O) ($C_0$–$C_4$ alkyl)-, $R^6S(C_0$–$C_4$ alkyl)-, $R^6S(=O)$ ($C_0$–$C_4$ alkyl)-, $R^6SO_2(C_0$–$C_4$ alkyl)-, $SO_2NR^6R^7$, $SiMe_3$, $R^6R^7$N($C_2$–$C_4$ alkyl)-, $R^6R^7$N($C_2$–$C_4$ alkoxy)-, $HSO_3$, HONH—, $R^6$ONH—, $R^8R^7$NNR$^6$—, HO(COR$^6$)N—, HO($R^6O_2$C)N, $C_2$–$C_6$ alkenyl, $C_3$–$C_{10}$ cycloalkyl, $C_3$–$C_{10}$ cycloalkyl, $C_3$–$C_{10}$ cycloalkylmethyl, aryl($C_1$–$C_4$alkyl)-, heteroaryl($C_0$–$C_4$alkyl)-, aryl($C_0$–$C_4$alkyl)O—, and heteroaryl($C_0$–$C_4$alkyl)O—, wherein said aryl groups are substituted with 0–2 substituents independently selected from a group consisting of $C_1$–$C_4$ alkyl, $C_1$–$C_4$ alkoxy, F, Cl, Br, $CF_3$, and $NO_2$;

$R^{15}$ is selected from the group consisting of H, halo, cyano, $C_1$–$C_8$ alkyl, $C_3$–$C_6$ alkenyl, and $C_3$–$C_{10}$ cycloalkyl($C_1$–$C_4$ alkyl)-, aryl($C_0$–$C_4$ alkyl)-, and heterocyclic($C_0$–$C_a$ alkyl)-, wherein said aryl or heterocyclic groups are substituted with 0–2 substituents independently selected from $R^{14}$;

$R^{16}$ is selected from the group consisting of H, halo, cyano, $C_1$–$C_8$ alkyl, $C_3$–$C_6$ alkenyl, $C_3$–$C_{10}$ cycloalkyl($C_0$–$C_4$ alkyl)-, aryl($C_0$–$C_4$ alkyl)-, and heterocyclic($C_0$–$C_4$ alkyl)-, wherein said aryl or heterocyclic groups are substituted with 0–2 substituents independently selected from $R^{14}$;

alternatively, when $R^{15}$ and $R^{16}$ are on adjacent carbon atoms [as in —HR$^{15}$C—CHR$^{16}$—], or when $R^{15}$ and $R^{16}$ are oriented on the same side of the double bond [as in the following structure (III)

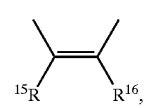

(III)]

$R^{15}$ and $R^{16}$ can be taken together with the carbon atoms to which they are attached to form a 3–7 membered carbocyclic aromatic or nonaromatic ring system, or a 3–7 membered heterocyclic aromatic or nonaromatic ring system, said carbocyclic or heterocyclic ring being optionally substituted with 0–2 substituents independently selected from the group consisting of $C_1$–$C_4$ alkyl, $C_1$–$C_4$ alkoxy, F, Cl, Br, $CF_3$, $NO_2$.

$R^{17}$ is selected from the group consisting of H, $C_1$–$C_8$ alkyl, $C_3$–$C_6$ alkenyl, $C_3$–$C_{10}$ cycloalkyl($C_0$–$C_4$ alkyl)-, $C_1$–$C_6$ alkylcarbonyl, $C_1$–$C_6$ alkylsulfonyl, $C_3$–$C_7$ cycloalkyl($C_0$–$C_5$ alkyl)carbonyl, $C_1$–$C_6$ alkoxycarbonyl, $C_3$–$C_7$ cycloalkyl($C_0$–$C_5$ alkoxy)carbonyl, hydroxy($C_2$–$C_4$)alkyl-, $C_1$–$C_3$ alkoxy($C_2$–$C_4$)alkyl-, ($C_0$–$C_4$ alkyl) ($C_0$–$C_4$ alkyl) amino($C_2$–$C_4$)alkyl-, aryl($C_0$–$C_4$ alkyl)-, aryl($C_1$–$C_5$ alkoxy)carbonyl, arylsulfonyl, heterocyclic($C_0$–$C_4$ alkyl), heterocyclic($C_1$–$C_5$ alkoxy)carbonyl, and heterocyclicsulfonyl, wherein said aryl or heterocyclic groups are substituted with 0–2 substituents independently selected from the group consisting of $C_1$–$C_4$ alkyl, $C_1$–$C_4$ alkoxy, $C_1$–$C_4$ alkoxy $C_1$–$C_4$ alkyl, oxo, F, Cl, Br, $CF_3$, CN, and $NO_2$;

$R^{18}$ is selected from the group consisting of H, $C_1$–$C_8$ alkyl, $C_3$–$C_6$ alkenyl, $C_3$–$C_{10}$ cycloalkyl($C_0$–$C_4$ alkyl)-, aryl($C_0$–$C_4$ alkyl)-, and heterocyclic($C_0$–$C_4$ alkyl), wherein said aryl or heterocyclic groups are substituted with 0–2 substituents independently selected from the group consisting of $C_1$–$C_4$ alkyl, $C_1$–$C_4$ alkoxy, F, Cl, Br, $CF_3$, CN, and $NO_2$; and alternatively, $R^{17}$ and $R^{18}$, when both are on the same nitrogen atom [as in (—$NR^{12}R^{13}$)] can be taken together with the nitrogen atom to which they are attached to form a heterocycle selected from 1-aziridinyl, 1-azetidinyl, 1-piperidinyl, 1-morpholinyl, 1-pyrrolidinyl, thiamorpholinyl, thiazolidinyl, and 1-piperazinyl, said heterocycle being optionally substituted with 0–3 groups selected from oxo, $C_1$–$C_6$ alkyl, $C_3$–$C_7$ cycloalkyl($C_0$–$C_4$ alkyl)-, $C_1$–$C_6$ alkylcarbonyl, ($C_1$–$C_6$ alkylcarbonyl)($C_0$–$C_4$alkyl)amino-, $C_3$–$C_7$ cycloalkyl($C_0$–$C_5$ alkyl)carbonyl, $C_1$–$C_6$ alkoxycarbonyl, $C_3$–$C_7$ cycloalkyl($C_0$–$C_5$ alkoxy)carbonyl, aryl($C_0$–$C_5$ alkyl), heterocyclic($C_0$–$C_5$ alkyl), aryl($C_1$–CS alkoxy)carbonyl, heterocyclic ($C_1$–$C_5$ alkoxy)carbonyl, $C_1$–$C_6$ alkylsulfonyl arylsulfonyl and heterocyclicsulfonyl, wherein said aryl or heterocyclic groups are substituted with 0–2 substituents independently selected from the group consisting of $CH_3$—, alkoxy, F, Cl, Br, $CF_3$, CN, and $NO_2$.

Preferred are compounds of Formula I, including stereoisomeric forms thereof, tautomeric forms thereof, pharmaceutically acceptable salt forms thereof, or prodrug forms thereof, wherein:

Z is either a 5, 6 or 7 membered monocyclic ring system substituted with $R^3$ or $R^4$ and optionally substituted with 0–4 substituents chosen from $R^1$ or $R^2$, or a 9 or 10 membered bicyclic ring system optionally substituted with 0–5 substituents chosen from $R^1$, $R^2$, $R^3$ or $R^4$, said ring systems optionally contain up to 4 heteroatoms selected from N, O, and S, and wherein a $CH_2$ adjacent to any of the said N, O or S heteroatoms is optionally substituted with oxo (=O);

$R^3$ is a 5- or 6-membered heterocyclic ring system containing up to 4 heteroatoms selected from N, O, and S, said heterocyclic ring system being optionally substituted with 0–1 $R^5$, wherein when $R^5$ is hydroxy the heterocycle may undergo tautomerization to an oxo species or may exist as an equilibrium mixture of both tautomers;

J and K are taken together to be selected from: —NHC(=O)—, —NHCHR$^9$—, and —C(=O)NH—;

X is selected from the group consisting of OR$^{12}$, NR$^{12}$R$^{13}$, $C_3$–$C_{10}$ cycloalkyl($C_0$–$C_4$ alkyl)-, $C_6$–$C_{10}$ aryl($C_0$–$C_4$ alkyl)-, and heterocyclic($C_0$–$C_4$ alkyl)-, wherein said aryl or heterocyclic groups are substituted with 0–3 substituents independently selected from $R^{14}$, with the proviso that when L is a single bond, X cannot be NR$^{12}$R$^{13}$;

$R^{12}$ is selected from the group consisting of ethyl, $C_3$–$C_{10}$ cycloalkyl($C_0$–$C_4$ alkyl)-, monocyclic or bicyclic aryl($C_0$–$C_4$ alkyl)-, and monocyclic or bicyclic 5–10 membered heterocyclic($C_0$–$C_4$ alkyl)-, and —CZ$^1$Z$^2$Z$^3$, wherein said aryl or heterocyclic groups are substituted with 0–3 substituents independently selected from $R^{14}$;

and all other constituents are as previously described.

All references cited herein are incorporated by reference in their entirety.

In the description above and elsewhere in the specification, including the claims, each occurrence of a particular constituent is independent of each other occurrence of that same constituent.

Listed below are definitions of various terms used in the specification and claims to describe the present invention.

The term "alkyl" refers to straight or branched chain alkyl.

The term "$C_{integer}$—$C_{integer}$" refers to a variable number of carbon atoms in a group depending on the integer values, as in $C_0$–$C_4$alkyl, which is meant to indicate a straight or branched alkyl group containing 0–4 carbon atoms. A group with 0 (zero) carbon atoms indicates that the carbon atom is absent i.e. there is a direct bond connecting adjacent terms. For example the term "$C_0$–$C_4$ alkylhydroxy" in the case "$C_0$" is meant to indicate the group hydroxy.

The term "halogen" or "halo" refers to fluorine, chlorine, bromine or iodine.

The term "aryl" refers to monocyclic or bicyclic aromatic hydrocarbons having 6 to 12 carbon atoms in the ring portion, such as phenyl, naphthyl, biphenyl and diphenyl groups which may be optionally substituted.

The term "alkenyl" refers to straight or branched chain alkenyl groups.

The term "alkynyl" refers to straight or branched chain alkynyl.

The term "cycloalkyl" refers to an optionally substituted, saturated cyclic hydrocarbon ring system.

The term "monocyclic" or bicyclic" refers to either a "carbocyclic" or a "heterocyclic" ring system.

The term "carbocyclic" refer to an optionally substituted, fully saturated or unsaturated, aromatic or nonaromatic cyclic group, which is a 3 to 7 membered monocyclic, or a 7 to 11 membered bicyclic, and all the atoms in the ring are carbon atoms. Exemplary groups include phenyl, naphthyl, anthracenyl, cyclohexyl, cyclohexenyl and the like.

The terms "heterocycle" and "heterocyclic" refer to an optionally substituted, fully saturated or unsaturated, aromatic or nonaromatic cyclic group, which is a 3 to 7 membered monocyclic, or a 7 to 11 membered bicyclic, which have at least one heteroatom and at least one carbon atom in the ring. Each heterocyclic ring may contain 1, 2, 3, or 4 heteroatomns selected from nitrogen, oxygen and sulfur, where the nitrogen and sulfur heteroatoms may also optionally be oxidized and the nitrogen heteroatoms may also optionally be quaternized. The heterocyclic group may be attached via a nitrogen or carbon atom.

Exemplary monocyclic heterocyclic groups include pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furanyl, tetrahydrofuranyl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydrothiopyranyl, tetrahydropyranyl, morpholinyl, thiamorpholinyl, thiamorpholinyl sulfoxide, tetrahydrothiopyranylsulfone, thiamorpholinyl sulfone, 1,3-dioxolane, tetrahydro-1,1-dioxothienyl, dioxanyl, isothiazolidinyl, thietanyl, thiiranyl, triazinyl, triazolyl, and the like.

Exemplary bicyclic heterocyclic groups include benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuranyl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b] pyridinyl), pyrrolo[l1,2-a]pyridinyl, 1,3-dioxindanyl, dihydroisoindolyl, dihydroquinazolinyl (such as 3,4-dihydro-4-oxo-quinazolinyl), benzisothiazolyl, benzisoxazolyl, benzodiazinyl, benzothiopyranyl, benzotriazolyl, benzpyrazolyl, dihydrobenzofuranyl, dihydrobenzothienyl, dihydrobenzothiopyranyl, dihydrobenzothiopyranyl sulfone, dihydrobenzopyranyl, indolinyl, indolyl, isochromanyl, isoindolinyl, naphthyridinyl, phthalazinyl, piperonyl, purinyl, pyridopyridyl, quinazolinyl, tetrahydroquinolinyl, thienoftiryl, thienopyridyl, thienothienyl, and the like.

"IMPDH-associated disorders" refers to any disorder or disease state in which inhibition of the enzyme IMPDH (inosine monophosphate dehydrogenase, EC1.1.1.205, of which there are presently two known isozymes referred to as IMPDH type 1 and IMPDH type 2) would modulate the activity of cells (such as lymphocytes or other cells) and thereby ameliorate or reduce the symptoms or modify the underlying cause(s) of that disorder or disease. There may or may not be present in the disorder or disease an abnormality associated directly with the IMPDH enzyme. Examples of IMPDH-associated disorders include transplant rejection and autoimmune disorders, such as rheumatoid arthritis, multiple sclerosis, juvenile diabetes, asthma, and inflammatory bowel disease, as well as inflammatory disorders, cancer and tumor disorders, T-cell mediated hypersensitivity diseases, ischemic or reperfusion injury, viral replication diseases, proliferative disorders and vascular diseases.

As used herein the term "treating" includes prophylactic and therapeutic uses, and refers to the alleviation of symptoms of a particular disorder in a patient, the improvement of an ascertainable measurement associated with a particular disorder, or the prevention of a particular immune response (such as transplant rejection). The term "patient" refers to a mammal, preferably a human.

The compounds of this invention may contain one or more asymmetric carbon atoms and thus may occur as racemates and racemic mixtures, single enantiomers, diastereomeric mixtures and individual diastereomers. All such isomers of the compounds disclosed herein are expressly included within the scope of the present invention. Each stereogenic carbon may be of the R or S configuration.

Combinations of substituents and variables thereof that result in stable compounds are also contemplated within the present invention. The term "stable" as used herein refers to compounds which possess stability sufficient to allow manufacture and which maintain their integrity for a sufficient period of time to be useful as a therapeutic or diagnostic agent.

As used herein, the compounds of this invention are defined to include pharmaceutically acceptable derivatives and prodrugs thereof. A "pharmaceutically acceptable derivative or prodrug" includes any pharmaceutically acceptable salt, ester, salt of an ester, or other derivative of a compound of the present invention which, upon administration to a subject, is capable of providing (directly or indirectly) a compound of the invention. Particularly favored derivatives and prodrugs are those that increase the bioavailability of the compounds of the present invention when such compound is administered to a subject (e.g., by allowing an orally administered compound to be more readily absorbed into the blood) or which enhance delivery of the parent compound to a biological compartment (e.g., the brain or lymphatic system) relative to the parent species. Preferred prodrugs include derivatives where a group that enhances aqueous solubility or active transport through the gut membrane is appended to a compound of the present invention.

Pharmaceutically acceptable salts of the compounds disclosed herein include those derived from pharmaceutically acceptable inorganic and organic acids and bases known to those skilled in the art. Examples of suitable acid salts include, but are not limited to, the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, metlianesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, trifluoroacetic, tosylate and undecanoate. Other acids, for example oxalic, while not in themselves pharmaceutically acceptable, may be employed in the preparation of salts useful as intermediates in obtaining the compounds of the present invention and their pharmaceutically acceptable acid additional salts.

Salts derived from appropriate bases include, but are not limited to, the following: alkali metal (e.g., sodium), alkaline earth metal (e.g., magnesium), ammonium and N—$(C_{1-4}$ alkyl$)_4^+$ salts. The present invention also envisions the quaternization of any basic nitrogen-containing groups of the compounds disclosed herein. Water- or oil-soluble or dispersible products may be obtained by such quaternization.

Methods of Preparation

The compounds of the present invention may be synthesized using conventional techniques known in the art. Advantageously, these compounds are conveniently synthesized from readily available starting materials. Following are general synthetic schemes for manufacturing compounds of the present invention. These schemes are illustrative and are not meant to limit the possible techniques one skilled in the art may use to manufacture compounds disclosed herein. Different methods will be evident to those skilled in the art. Additionally, the various steps in the synthesis may be performed in an alternate sequence or order to give the desired compound(s). All documents cited herein are incorporated herein by reference in their entirety.

Compounds of the present invention can be made by many methods, which will be known to one skilled in the art of organic chemistry. In general, the time taken to complete a reaction procedure will be judged by the person performing the procedure, preferably with the aid of information obtained by monitoring the reaction by methods such as HPLC or TLC. A reaction does not have to go to completion to be useful to this invention. The preparation of heterocycles useful to this invention are described in the series of books: "Comprehensive Heterocyclic Chemistry. The Structure, Reactions, Synthesis and Uses, of Heterocyclic Compounds" Katritzky, A. R., Rees, C. W. Ed's Pergamon Press New York, First edition 1984, and "Comprehensive Heterocyclic Chemistry II. A Review of the Literature 1982–1995. The Structure, Reactions, Synthesis and Uses, of Heterocyclic Compounds" Katritzky, A. R., Rees, C. W. and Scriven, E., F. Ed's Pergamon Press New York, 1996. In general the compounds of this invention can be prepared by the coupling of an appropriate amine or hydrazine with a carboxylic acid to provide the compounds of interest, alternatively the compounds may be prepared by simple alkylation of an amine or hydrazine, or reductive alkylation of an amine or hydrazine Examples of methods useful for the production of compounds of this invention are illustrated in schemes Ia-Vb.

Amines useful for the preparation of compounds useful to this invention may be commercially available or readily prepared by many methods known to one skilled in the art of organic chemistry, and are described in "Comprehensive Organic Transformations. A Guide to Functional Group Preparation." pp-385–439. Richard C. Larock 1989 VCH Publishers, Inc. Examples include but are not limited to, reduction of a nitro group, reduction of an azide and reduction of a nitrile.

A general method for the synthesis of the an amine useful in this invention can be perfomed by metal catalyzed cross coupling methods known in the literature. The simplest case is a Suzuki type cross coupling (Miyaura, N., Yanagi, T. Suzuki, A., Synth. Comm. 11(7):513–519 (1981); A. Suzuki et. al., J. Am. Chem. Soc. 111:513 (1989); and V. N. Kalinin, Russ. Chem. Rev. 60:173 (1991)) of an aryl boronic acid or ester (Ia. 1) (as shown below) with an appropriate bromo-heterocycle in the presence of a suitable catalyst such as tetrakis(triphenylphosphine) palladium. After the cross coupling has been performed the product may be deprotected. The choice of protecting group and its method of removal will be readily apparent to one skilled in the art of organic chemistry. Such considerations and methods are, for example, described by Greene, Theodora W. and Wuts, Peter G. M. in "Protective Groups in Organic Synthesis." 2nd Ed. (1991) Publisher: (John Wiley and Sons, Inc., New York, N.Y. For example, if the protecting group is acetyl the product may be deprotected by treatment with aqueous potassium hydroxide at a concentration of 0.5N to 5 N at room temperature to 100° C. for a period between 0.5 h and 24 h.

For example aryl boronic acid (Ia.5) may react with the known 5-bromothiazole (Ia.6) in the presence of tetrakis (triphenylphosphine) palladium (0), to provide (Ia.7) which may be deprotected by an appropriate method.

Scheme Ia

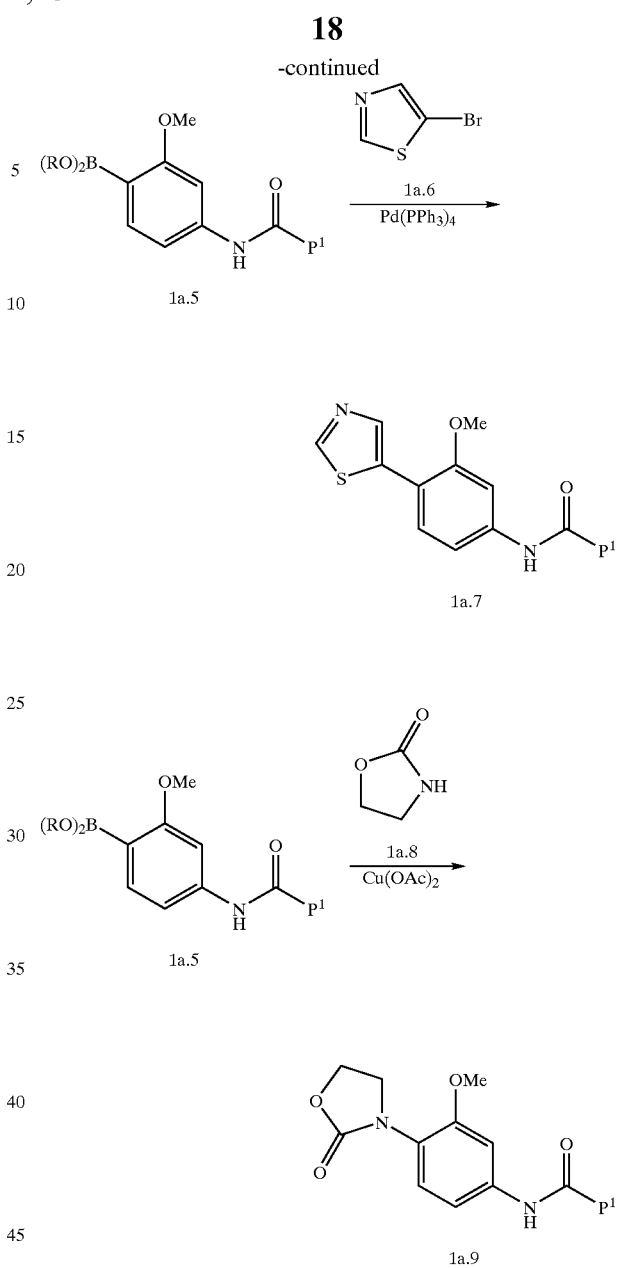

R=H, Alkyl
X=H, OMe, etc.
HET= a 5 or 6 membered ring containing at least one O, N, S atom with an unsaturated bond directly attached to the bromine
P¹=alkyl, O-benzyl, O-tertbutyl, etc.

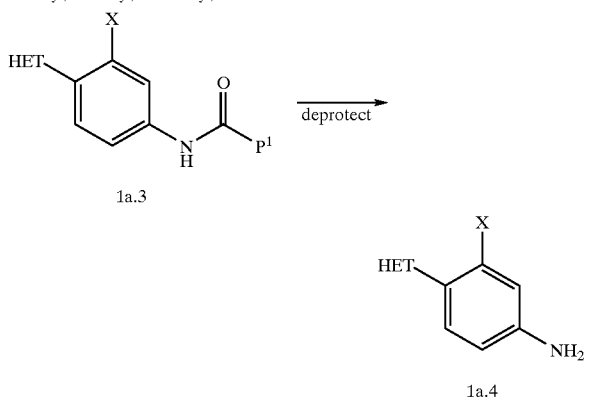

Copper has been recently been shown to be an effective catalyst for cross coupling of aryl boronic acids to N-unsubstituted heterocycles as described by Chan. et al., Tetrahed. Lett. 39:2933–2936 (1998); and Lam et al., Tetrahed. Lett. 39:2941–2944 (1998). This results in compounds in which the heterocycle is attached to the aryl ring through nitrogen rather than carbon. For example aryl boronic acid (Ia.5) may react with oxazolone (Ia.8) in the presence of copper (II) acetate in the presence of an amine base such as pyridine to provide intermediate (Ia.9) which may be deprotected by an appropriate method In general aryl boronic acids and esters, Ib.3, where X is not Br or I, may be prepared as shown in Scheme Ib, from the corresponding arylbromide (Ib.1) by treatment with a palladium catalyst such as [1,1'-Bis(diphenylphosphino)-ferrocene] dichloropalladium (II) and bis(pinacolato) diboron, (Ib.2), as reported by Ishayama et al., J. Org. Chem., (1995) 7508–7510. Aryl boronic esters may be converted to the corresponding boronic acid by several methods including treatment with aqueous HCl. In a variation of the synthesis, the nitrogen may be masked as a nitro group and later reduced by several means including metal reductions, such as by treatment with tin chloride in HCl or by refluxing the nitro compound with zinc in the presence of $CaCl_2$ in a solvent such as ethanol, or in certain cases the nitro group may be reduced by catalytic hydrogenation in the presence of catalysts such as palladium on carbon. The conditions for the reduction of nitro groups are detailed in several references including Hudlicky, M., "Reductions in Organic Chemistry", 2nd Ed., ACS Monograph 188, 1996, pp 91–101 American Chemical Society, Washington, D.C. A second variation of the synthesis allows the aryl bromide to remain through the entire synthesis and elaborated to the boronic acid at the end. This may eliminate the need for a protecting group.

Scheme Ib

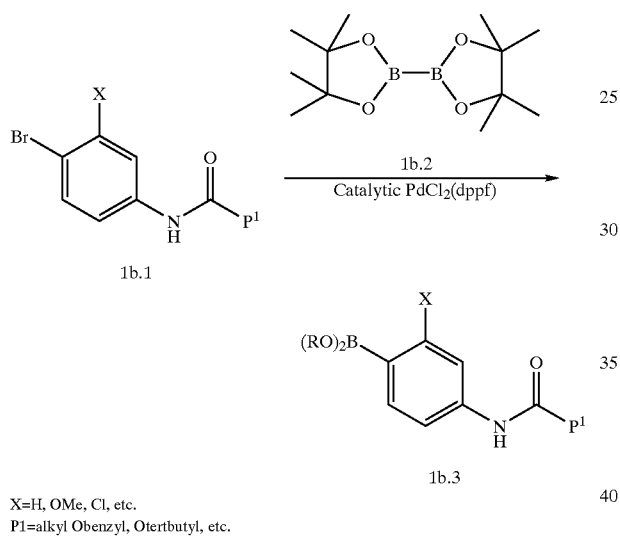

X=H, OMe, Cl, etc.
P1=alkyl Obenzyl, Otertbutyl, etc.

In certain cases it may be more expedient to construct the heterocyclic ring by other methods. A general method for the synthesis of 5-membered heterocycles includes the 1,3-dipolar cycloaddition reaction, which is well known to one skilled in the art of organic chemistry and is described by Padwa, Albert; Editor. in "1,3-Dipolar Cycloaddition Chemistry, Vol. 2" (1984) John Wiley and Sons, New York, N.Y.; and Padwa, Albert; Editor. in "1,3-Dipolar Cycloaddition Chemistry, Vol. 1" (1984) John Wiley and Sons, New York, N.Y. For example oxazoles may be prepared by 1,3 dipolar cycloaddtion of the corresponding aldehyde (Ic.1) and (p-tolylsulfonyl)methyl isocyanate (TOSMIC) (Ic.2) as shown in scheme Ic. The aldehyde may be commercially available or prepared from the corresponding methyl group by oxidation with reagents such as $CrO_3$, $MnO_2$, and ammonium cerium (IV) nitrate by methods well known to one skilled in the art of organic chemistry and is described in Hudlicky, M., "Oxidations in Organic Chemistry", ACS Monograph 186 (1990), American Chemical Society, Washington, D.C. The nitro group in intermediate (Ic.3), is reduced to an amine (Ic.4), as discussed above.

Scheme Ic

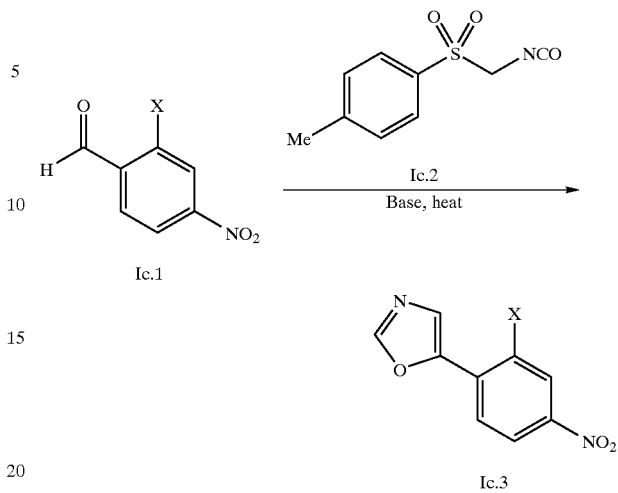

X=H, OMe, Br, Cl, etc.

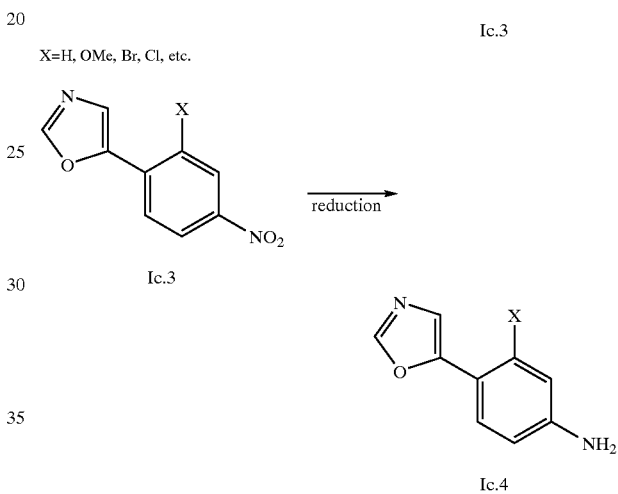

An alternative method of producing amines useful to this invention is by nucleophilic attack an electron deficient ring system as outlined in scheme Id. Halonitrobenzenes (Id.1), are either commercially available or readily prepared by methods known to one skilled in the art of organic synthesis. Displacement with a variety of nucleophiles produce compounds of structure (Id.2). In one example heating (Id.3) with a nucleophilic heterocycle such as triazole with or without the addition of a base provides the intermediate nitro compound which may be reduced as previously describe to provide amines (Id.4). Alternatively simple organic nucleophiles such as cyanide can be reacted with halonitrobenzene (Id.5) to provide an intermediate nitrocompound which can be reduced by many methods to amine (Id.6).

Scheme Id

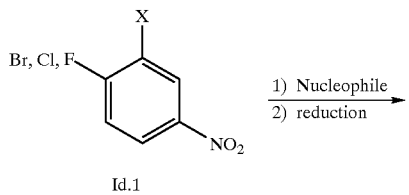

-continued

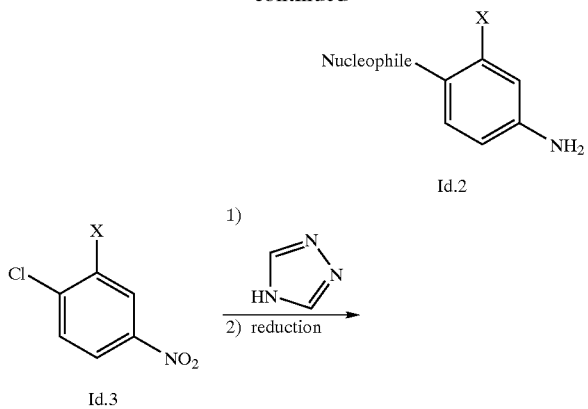

Scheme IIa, IIb, IIc, depicts the coupling of the amines prepared in Scheme Ia and Ib to various acids. The acids useful in this invention are either commercially available such as ethyl oxalyl chloride, ethyl malonyl chloride, chloroacetyl chloride, benzoyl formate or indol-2-yl carboxylic acid, or readily prepared by one skilled in the art of organic chemistry. Carboxylic acids may also be prepared by the hydrolysis of carbocylic acid esters. The coupling is carried out using any of the many methods for the formation of amide bonds known to one skilled in the art of organic synthesis. These methods include but are not limited to conversion of the acid to the corresponding acid chloride, or use of standard coupling procedures such as the azide method, mixed carbonic acid anhydride (isobutyl chloroformate) method, carbodiimide (dicyclohexylcarbodiimide, diisopropylcarbodiimide, or water-soluble carbodiimides) method, active ester (p-nitrophenyl ester, N-hydroxysuccinic imido ester) method, carbonyldlimidazole method, phosphorus reagents such as BOP-Cl. Some of these methods (especially the carbodiimide) can be enhanced by the addition of 1-hydroxybenzotriazole.

Thus amine (IIa.1) may be coupled with acid chloride (IIa.2) in the presence of an amine base such as triethylamine to produce amide (IIa.3). Ester (IIa.3) is also a useful intermediate. The ester may be hydrolized by treatment with aqueous base such as sodium hydroxide to produce acid (IIa.4). This acid can be coupled with a second amine to produce the bisamide (IIa.5). The amines useful to this invention are commercially available, or are readily prepared from commercial starting materials by one skilled in the art of organic chemistry.

Scheme IIa

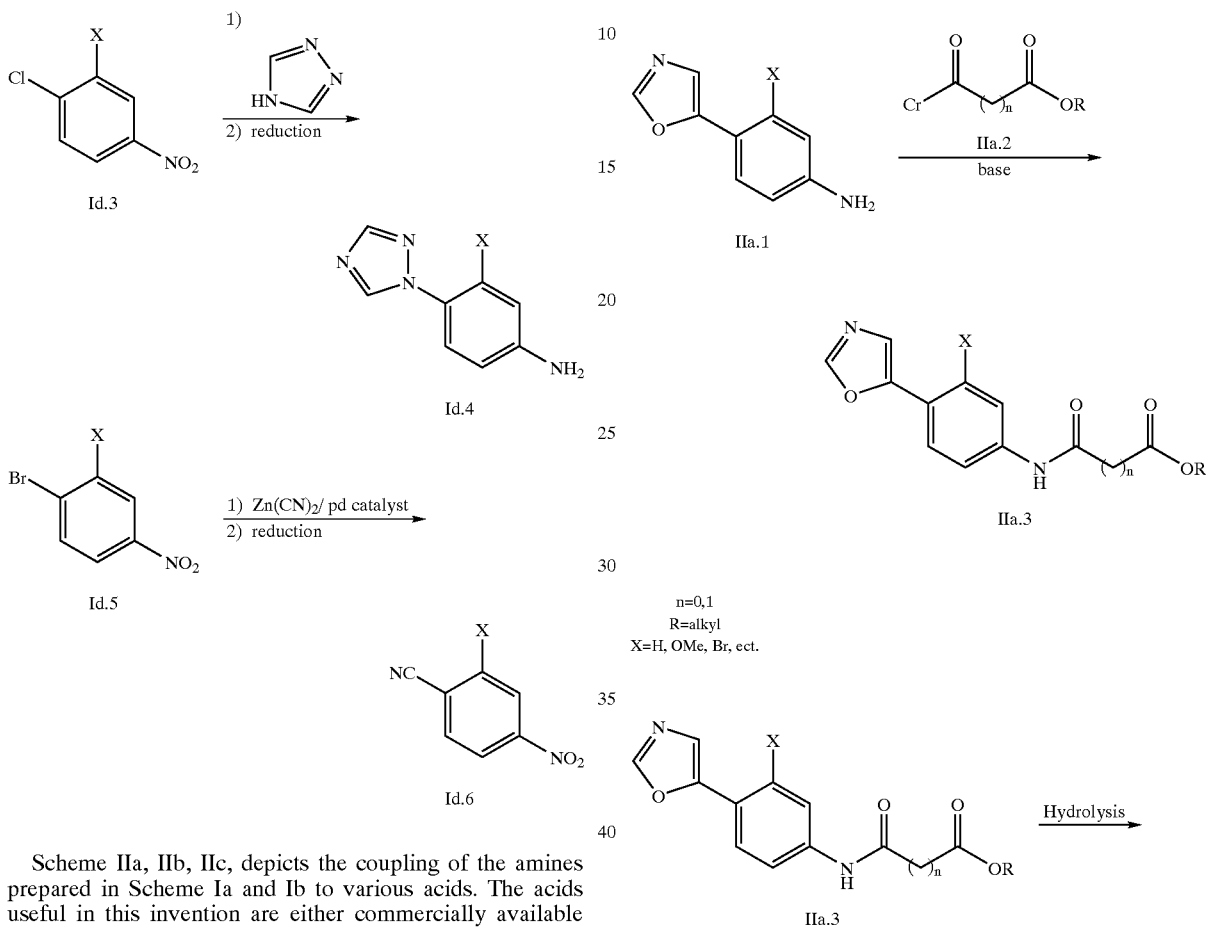

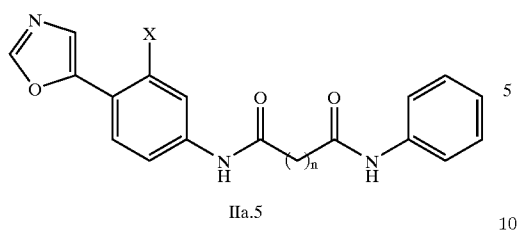

IIa.5

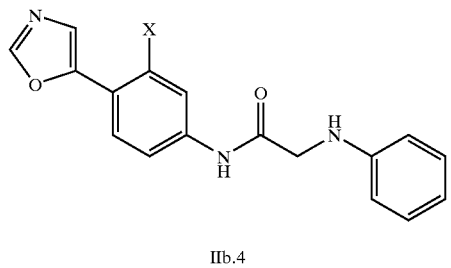

IIb.4

In the case of carboxylic acid derivatives which contain an □-halo atom, such as chlorine or bromine, the product may be used as an intermediate. Such reagents readily react with amines in the presence of a suitable base to provide □-aminoacids useful to this invention. For example in Scheme IIb, amine (IIb.1) is coupled with chloroacetyl chloride, (IIb.2), to produce intermediate (IIb.3) which can be heated in the presence of an amine with or without the addition of a base to provide compound (IIb.4).

Scheme IIc depicts the coupling of the amine to a heterocyclic acid. This can be accomplished with many of the coupling agents described previously. The heterocyclic carboxyiic acids are either commercially available or readily prepared by methods known to one skilled in the art of organic chemistry. For example many heterocycles undergo regioselective lithiation; this intermediate may be treated with $CO_2$ gas or solid to provide the required carboxylic acids. For example amine (IIc.1), may be coupled with acid (IIc.2) to provide the desired product (IIc.3).

Scheme IIb

Scheme IIc

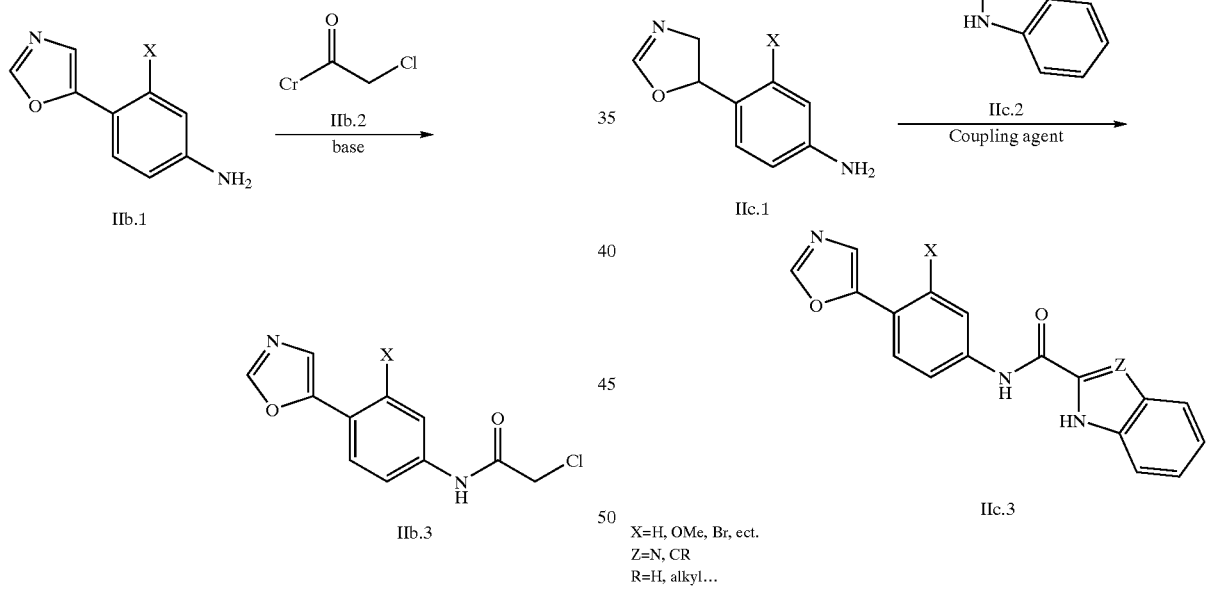

X=H, OMe, Br, ect.
Z=N, CR
R=H, alkyl...

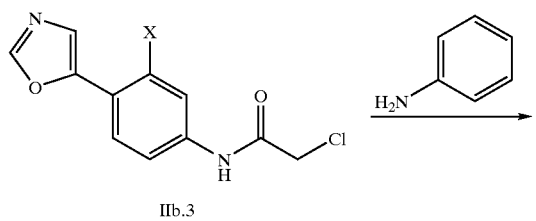

X=H, OMe, Br, ect.

Carboxylic acid derivative useful for this invention are either commercially available or readily prepared by one skilled in the art of organic chemistry. The preparation of carboxylic acids and related functional groups such as carboxylic acid esters are described in "Comprehensive Organic Transformations. A Guide to Functional Group Preparation." Richard C. Larock 1989 VCH Publishers, Inc. Carboxylic acids can be prepared by a number of methods not limited to ozonolysis of an alkene, ozonolysis of a furan ring, oxidation of a alkyl group when attached to an aryl ring, oxidation of a primary alcohol, hydrolysis of a nitrile, carbonylation procedures, and homologation or degradation of an existing carboxylic acid.

Scheme IIIa illustrates the preparation of a carboxylic acid derivative useful as an intermediate for this invention. The preparation of methyl 4-formyl-3-methoxybenzoate (IIIa.1) has been reported by Griera, R. et al. in European Journal of Medicinal Chemistry (1997) pp 547–570. Reaction of the aldehyde with TOSMIC as described in scheme Ic, followed by acidification precipitates the desired acid.

Scheme IIIa

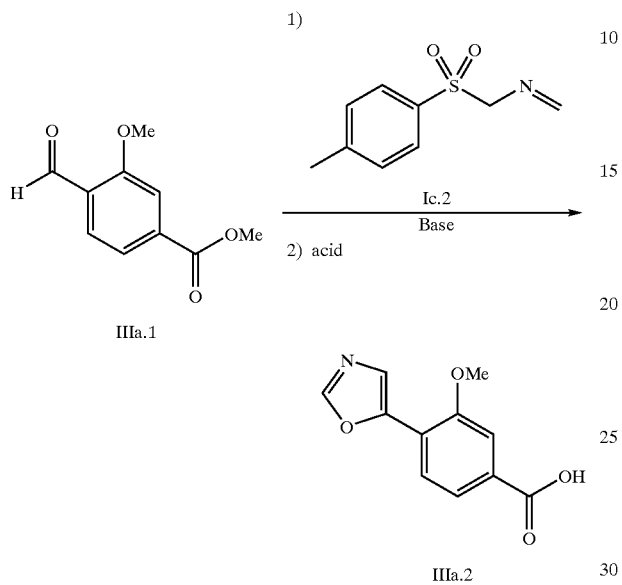

Hydrazines useful as intermediates in this invention are either commercially available or may be prepared by many methods known to one skilled in the art of organic synthesis including reduction of diazonium salts as illustrated in scheme IVa.

Scheme IVa

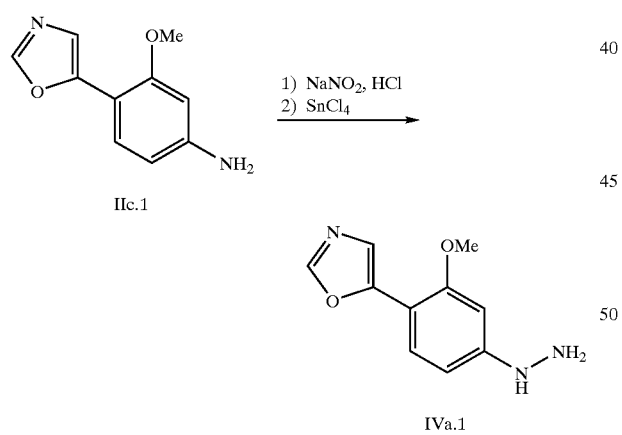

Aldehydes and ketones useful as intermediates in this invention are either commercially available or may be readily prepared by many methods known to one skilled in the art of organic synthesis and are illustrated in "Comprehensive Organic Transformations. A Guide to Functional Group Preparation." Richard C. Larock 1989 VCH Publishers, Inc. Examples of methods for production of aldehydes include but are not limited to oxidation of a primary alcohol, reduction of carboxylic acid ester, or ozonolysis of an alkene. Examples of methods for production of ketones include but are not limited to oxidation of secondary alcohols, and oxidative cleavage of alkenes.

Compounds useful to this invention may also be prepared by reductive amination using either amines or hydrazines and an aldehyde. A useful method of performing reductive aminations has been described by Abdel-Magid, A. F., et al in Journal of Organic Chemistry (1996) pp 3849–3862. This method involves dissolving the aldehyde or ketone and an amine or hydrazine in a suitable solvent such as 1,2-dichloroethane in the presence of sodium triacetoxyborohydride. Reductive amination is illustrated in scheme Va.

Scheme Va.

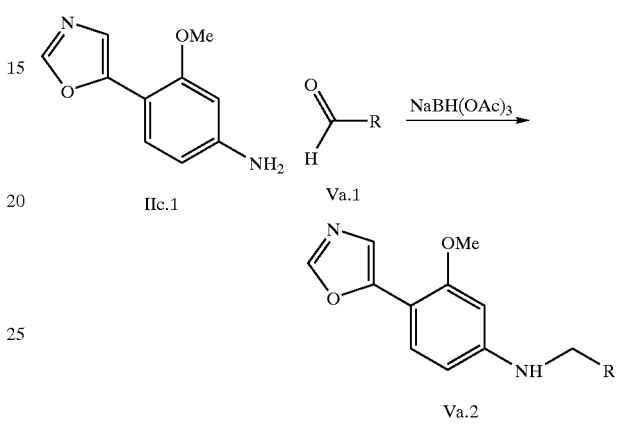

Scheme Vb illustrates alkylation as a means of forming the nitrogen carbon bond. Amine (Iic.1) may be readily alkylated by □-haloamides, by heating in a solvent such as N,N-dimethylfonnamide with or without the addition of a base such as potassium carbonate to provide compounds of type (Vb.1). Alkylation of amine (Iic.1) with an allylic halide in a solvent such as N,N-dimethylformamide in the presence or absence of a base provides the alkylated compounds (Vb.2) The reactions illustrated in scheme Vb, generally require purification by a method such as flash column chromatogaphy or prepraratory high performance liquid chormnatography (HPLC) to provide the desired product. Such methods would be known to one skilled in the art of organic chemistry.

Scheme Vb

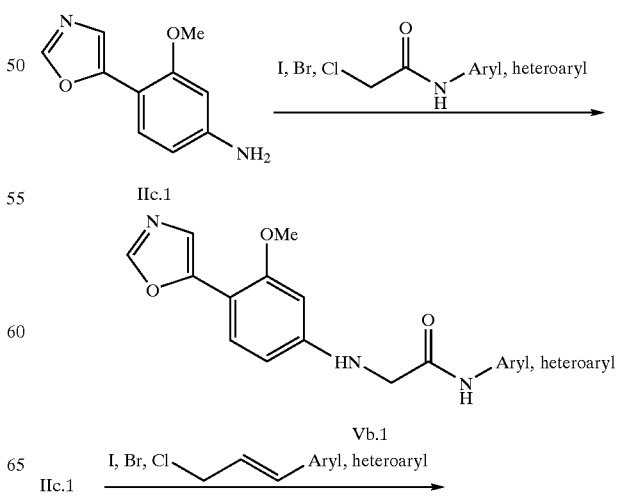

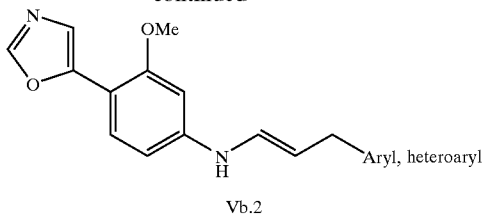

Vb.2

The compounds of the present invention inhibit IMPDH enzyme, and are thus useful in the treatment, including prevention and therapy, of disorders which are mediated or effected by cells which are sensitive to IMPDH inhibition, as described previously. The present invention thus provides methods for the treatment of IMPDH-associated disorders, comprising the step of administering to a subject in need thereof at least one compound of the formula I, in an amount effective therefor. Other therapeutic agents, such as those described below, may be employed with the inventive compounds in the present methods. In the methods of the present invention, such other therapeutic agent(s) may be administered prior to, simultaneously with or following the administration of the compound(s) of the present invention.

Use of the compounds of the present invention in treating exemplified by, but is not limited to, treating a range of disorders such as: treatment of transplant rejection (e.g., kidney, liver, heart, lung, pancreas (e.g., islet cells), bone marrow, cornea, small bowel, skin allografts, skin homografts (such as employed in burn treatment), heart valve xenografts, serum sickness, and graft vs. host disease, in the treatment of autoimmune diseases, such as rheumatoid arthritis, psoriatic arthritis, multiple sclerosis, juvenile diabetes, asthma, inflammatory bowel disease (such as Crohn's disease and ulcerative colitus), pyoderma gangrenum, lupus (systemic lupus erythematosis), myasthenia gravis, psoriasis, dermatitis, dermatomyositis; eczema, seborrhoea, pulmonary inflammation, eye uveitis, hepatitis, Grave's disease, Hashimoto's thyroiditis, autoimmune thyroiditis, Behcet's or Sjorgen's syndrome (dry eyes/mouth), pernicious or immunohaemolytic anaemia, Addison's disease (autoimmune disease of the adrenal glands), idiopathic adrenal insufficiency, autoimmune polyglandular disease (also known as autoimmune polyglandular syndrome), glomerulonephritis, scleroderma, morphea, lichen planus, viteligo (depigmentation of the skin), alopecia areata, autoimmune alopecia, autoimmune hypopituatarism, Guillain-Barre syndrome, and alveolitis; in the treatment of T-cell mediated hypersensitivity diseases, including contact hypersensitivity, delayed-type hypersensitivity, contact dermatitis (including that due to poison ivy), uticaria, skin allergies, respiratory allergies (hayfever, allergic rhinitis) and gluten-sensitive enteropathy (Celiac disease); in the treatment of inflammatory diseases such as osteoarthritis, acute pancreatitis, chronic pancreatitis, asthma, acute respiratory distress syndrome, Sezary's syndrome and vascular diseases which have an inflammatory and or a proliferatory component such as restenosis, stenosis and artherosclerosis; in the treatment of cancer and tumor disorders, such as solid tumors, lymphomas and leukemia; in the treatment of fungal infections such as mycosis fungoides; in protection from ischemic or reperfusion injury such as ischemic or reperfusion injury that may have been incurred during organ transplantation, myocardial infarction, stroke or other causes; in the treatment of DNA or RNA viral replication diseases, such herpes simplex type 1 (HSV-1), herpes simplex type 2 (HSV-2), hepatitis (including hepatitis B and hepatitis C) cytomegalovirus, Epstein-Barr, and human immunodeficiency virus (HIV).

Additionally, IMPDH is also known to be present in bacteria and thus may regulate bacterial growth. As such, the IMPDH-inhibitor compounds of the present invention may be useful in treatment or prevention of bacterial infection, alone or in combination with other antibiotic agents.

In a particular embodiment, the compounds of the present invention are useful for the treatment of the aforementioned exemplary disorders irrespective of their etiology, for example, for the treatment of transplant rejection, rheumatoid arthritis, inflammatory bowel disease, and viral infections.

The present invention also provides pharmaceutical compositions comprising at least one of the compounds of formula I, or a salt thereof, capable of treating an IMPDH-associated disorder in an amount effective therefor, alone or in combination with at least one additional therapeutic agent, and any pharmaceutically acceptable carrier, adjuvant or vehicle. "Additional therapeutic agents" encompasses, but is not limited to, an agent or agents selected from the group consisting of an immunosuppressant, an anti-cancer agent, an anti-viral agent, an anti-inflammatory agent, an anti-fungal agent, an antibiotic, or an anti-vascular hyper-proliferation compound.

The term "pharmaceutically acceptable carrier, adjuvant or vehicle" refers to a carrier, adjuvant or vehicle that may be administered to a subject, together with a compound of the present invention, and which does not destroy the pharmacological activity thereof. Pharmaceutically acceptable carriers, adjuvants and vehicles that may be used in the pharmaceutical compositions of the present invention include, but are not limited to, the following: ion exchangers, alumina, aluminum stearate, lecithin, self-emulsifying drug delivery systems ("SEDDS") such as d(-tocopherol polyethyleneglycol 1000 succinate), surfactants used in pharmaceutical dosage forms such as Tweens or other similar polymeric delivery matrices, serum proteins such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β- and γ-cyclodextrin, or chemically modified derivatives such as hydroxyalkylcyclodextrins, including 2- and 3-hydroxypropyl-β-cyclodextrins, or other solubilized derivatives may also be used to enhance delivery of the compounds of the present invention.

The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the formula I may be administered by any suitable means, for example, orally, such as in the form of tablets, capsules, granules or powders; sublingually; buccally; parenterally, such as by subcutaneous, intravenous, intramuscular, or intrastemal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present compounds may also be administered liposomally.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The present compounds may also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid. The term "parenteral" as used herein includes subcutaneous, intracutaneous, intravenous, intramuscular, intraarticular, intraarterial, intrasynovial, intrastemal, intrathecal, intralesional and intracranial injection or infusion techniques.

Exemplary compositions for rectal administration include suppositories which may contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

The effective amount of a compound of the present invention may be determined by one of ordinary skill in the art, and includes exemplary dosage amounts for an adult human of from about 0.1 to 500 mg/kg of body weight of active compound per day, which may be administered in a single dose or in the form of individual divided doses, such as from 1 to 5 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to IMPDH-associated disorders.

The compounds of the present invention may be employed alone or in combination with each other and/or other suitable therapeutic agents useful in the treatment of IMPDH-associated disorders, such as IMPDH inhibitors other than those of the present invention, immunosuppressants, anti-cancer agents, anti-viral agents, anti-inflammatory agents, anti-fuligal agents, antibiotics, or anti-vascular hyperproliferation agents.

Exemplary such other therapeutic agents include the following: cyclosporins (e.g., cyclosporin A), CTLA4-Ig, antibodies such as anti-ICAM-3, anti-IL-2 receptor (Anti-Tac), anti-CD45RB, anti-CD2, anti-CD3 (OKT-3), anti-CD4, anti-CD80, anti-CD86, monoclonal antibody OKT3, agents blocking the interaction between CD40 and CD154 (a.k.a. "gp39"), such as antibodies specific for CD40 and/or CD154, fusion proteins constructed from CD40 and/or CD154/gp39 (e.g., CD40Ig and CD8gp39), inhibitors, such as nuclear translocation inhibitors, of NF-kappa B function, such as deoxyspergualin (DSG), non-steroidal antiinflammatory drugs (NSAIDs) such as ibuprofen, celecoxib and rofecoxib, steroids such as prednisone or dexamethasone, gold compounds, antiviral agents such as abacavir, antiproliferative agents such as methotrexate, lellunomide, FK506 (tacrolimus, Prograf), cytotoxic drugs such as azathiprine and cyclophosphamide, TNF-α inhibitors such as tenidap, anti-TNF antibodies or soluble TNF receptor, and rapamycin (sirolimus or Rapamune) or derivatives thereof.

The above other therapeutic agents, when employed in combination with the compounds of the present invention, may be used, for example, in those amounts indicated in the Physicians' Desk Reference (PDR) or as otherwise determined by one of ordinary skill in the art.

The compounds disclosed herein are capable of targeting and inhibiting IMPDH enzyme. Inhibition can be measured by various methods, including, for example, IMP dehydrogenase HPLC assays (measuring enzymatic production of XMP and NADH from IMP and AND) and IMP dehydrogenase spectrophotometric assays (measuring enzymatic production of NADH from AND). See, e.g., Montero et al., Clinica Chimica Acta 238:169–178 (1995). Additional assays known in the art can be used in ascertaining the degree of activity of a compound ("test compound") as an IMPDH inhibitor. The inventors used the following assay to determine the degree of activity of the compounds disclosed herein as IMPDH inhibitors:

Activity of IMPDH I and IMPDH II was measured following an adaptation of the method described in WO 97/40028. The reaction mixture was prepared containing 0.1M Tris pH 8.0, 0.1 M KCl, 3 mM EDTA, 2 mM DTT, 0.4 mM IMP and 40 nM enzyme (IMPDH I or IMPDH II). The reaction was started by the addition of AND to a final concentration of 0.4 mM. The enzymatic reaction was followed by measuring the increase in absorbance at 340 nM that results from the formation of NADH. For the analysis of potential inhibitors of the enzyme, compounds were dissolved in DMSO to a final concentration of 10 mM and added to the assay mixture such that the final concentration of DMSO was 2.5%. The assay was carried out in a 96-well plate format, with a final reaction volume of 200 □l.

The compounds disclosed herein are capable of inhibiting the enzyme IMPDH at a measurable level, under the above-described assay or an assay which can determine an effect of inhibition of the enzyme IMPDH.

The following examples illustrate preferred embodiments of the present invention and do not limit the scope of the present invention, which is defined in the claims. Abbreviations employed in the Examples are defined below. Compounds of the Examples are identified by the example and step in which they are prepared (e.g., "1A" denotes the title compound of Example 1A), or by the example only where the compound is the title compound of the example (for example, "2" denotes the title compound of Example 2).

| Abbreviations | |
| --- | --- |
| Ac | Acetyl |
| AcOH | Acetic acid |
| aq. | Aqueous |
| CDI | Carbonyldiimidazole |
| Bn | Benzyl |
| Boc | tert-butoxycarbonyl |
| DMAP | Dimethylaminopyridine |
| DMF | dimethylformamide |
| DMSO | Dimethylsulfoxide |
| EDC | 1-(3-Dimethylaminopropyl)-3-ethylcarbodiimide hydrochloride |
| EtOAc | Ethyl acetate |
| Et | Ethyl |
| EtOH | Ethanol |
| h | Hours |
| i | iso |
| HPLC | High pressure liquid chromatography |
| HOAc | Acetic acid |
| THF | Tetrahydrofuran |
| Lawesson's Reagent | [2,4-bis(4-methoxyphenyl)-1,3-dithia-2,4-diphosphetane-2-4-disufide |
| LC | liquid chromatography |
| Me | Methyl |
| MeOH | Methanol |
| min. | Minutes |
| $M^+$ | $(M + H)^+$ |
| $M^{+1}$ | $(M + H)^+$ |
| MS | Mass spectrometry |
| n | normal |
| Pd/C | Palladium on carbon |
| Ph | Phenyl |
| Pr | Propyl |
| Ret Time | Retention time |
| rt or RT | Room temperature |
| sat. | Saturated |
| TFA | Trifluoroacetic acid |
| THF | Tetrahydrofuran |
| TOSMIC | Tosylmethyl isocyanide |
| YMC | YMC Inc, Wilmington, NC 28403 |

General:

The following LC/MS conditions were utilized: LC/MS condition A, denoted as "ret. time[A]": Column: YMC S5 ODS Ballistic column, 4.6×50 mm; 0% B–100% B, linear gradient over 4 min at 4.0 ml/min; 1 min isocratic at 100% B; Solvent A: 10% MeOH-90% $H_2O$-0.1% TFA; Solvent B: 90% MeOH-10% $H_2O$-0.1% TFA.

LC/MS condition B, denoted as "ret. time[B]": Column: Shimadzu 4.6×50 mm Ballistic, 0% B–100% B, linear gradient over 4 min at 4.0 ml/min; 1 min isocratic at 100% B. Solvent A=10% MeOH, 90% $H_2O$, 0.1% TFA. Solvent B=90% MeOH, 10% $H_2O$, 0.1% TFA.

EXAMPLE 1

N-(4-Fluorophenyl)-N2-[3-methoxy-4-(5-oxazolyl) phenyl]glycinamide

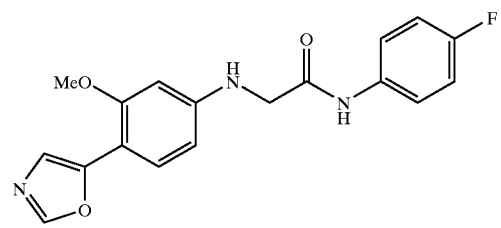

1A. 4-Nitro-2-methoxy-(α,α-bisacetoxy)toluene

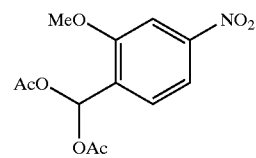

To a 5 L three necked round bottom flask equipped with a mechanical stirrer was added 4-nitro-2-methoxytoluene (150.0 g, 0.8973 mol), HOAc (900 mL) and $Ac_2O$ (900 mL). The mixture was stirred and cooled to 8° C. with an acetone/ice bath. Concentrated $H_2SO_4$ (136 mL) was carefully added while keeping the pot temperature <19° C. After cooling to 0° C., $CrO_3$ (252.6 g, 2.526 mol, 2.815 equiv.) was added portion-wise over 1 hour while maintaining the reaction temperature between 0–10° C. After the addition, the mixture was stirred at 0° C. for 30 minutes at which time the reaction was complete. The reaction mixture was then carefully poured into ice (1.5 kg) with stirring to give a slurry. The remaining black gummy residue was rinsed with HOAc (3×100 mL), and the washes were added to the slurry. After stirring for 10 minutes, the slurry was filtered. The cake was washed with water (3×400 mL) and suction dried for 17 hours to give 1A (129.0 g, 51%). $^1$H NMR ($CDCl_3$) d 8.02 (s, 1H), 7.89 (d, J=8.4 Hz, 1H), 7.77 (s, 1H), (d, 8.4 Hz, 1H), 3.98 (s, 3H), 2.16 (s, 6H).

1B. 4-Nitro-2-methoxybenzaldehyde

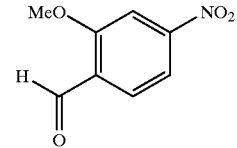

To a 2 L rounded bottom flask equipped with a condenser and a mechanical stirrer was placed 1A (250.7 g, 0.8851 mol), dioxane (300 mL) and concentrated HCl (60 mL). The reaction mixture was heated to reflux and stirred under $N_2$ for 20 hours. Water (250 mL) was added dropwise while maintaining the reaction mixture at reflux. After cooling to 0° C. with an ice/water bath, the resulting slurry was stirred for 30 minutes and then filtered. The cake was washed with water (4×200 mL) and suction dried for 17 hours to give 1B (I146.3 g, 91%) as yellow solid. $^1$H NMR ($CDCl_3$) d 10.54

(s, 1H), 8.00 (d, J=8.3 Hz, 1H), 7.91 (s, 1H), 7.89 (d, J=8.3 Hz, 1H), 4.08 (s, 3H).

1C. 5-(4-Nitro-2-methoxyphenyl)oxazole

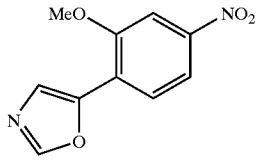

To a 5 L three necked round bottom flask equipped with a condenser and a mechanical stirrer was placed 1B (146.3 g, 0.8076 mol), TOSMIC (157.7 g, 0. 8077 mol), $K_2CO_3$ (116.6 g, 0.8075 mol) and MeOH (2.5 L). The mixture was heated to reflux under $N_2$ and stirred for 3 hours. Water (1.25 L) was added drop-wise while maintaining the pot temperature between 59–69° C. The resulting slurry was cooled to room temperature, and then to 5° C. with an ice-water bath. After stirring for 30 minutes at 5° C., the slurry was filtered. The resulting cake was washed with water (3×400 mL) and dried in a vacuum oven at 45° C. for 20 hours to give 1C (148.5 g, 84%) as a yellow-reddish solid. $^1$H NMR (CDCl$_3$) d 8.02 (s, 1H), 7.97 (d, J=2 Hz, 1H), 7.95 (d, J=2 Hz, 1H), 7.86 (s, 1H), 7.78 (s, 1H), 4.11 (s, 3H).

1D. 5-(4-Amino-2-methoxyphenyl)oxazole

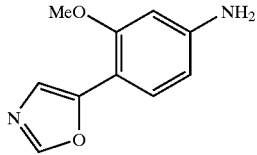

In a 2 L hydrogenation flask was placed 1C (130.0 g, 0.6131 mol), Pd/C (10%, 26.2 g) and absolute EtOH (1280 mL). The mixture was hydrogenated at 35–45 psi $H_2$ until the reaction was complete. The mixture was filtered over a pad of celite (20 g) and the cake was washed with EtOH (3×100 mL). The filtrate was concentrated to a volume of 350 mL. Heptane (500 mL) was added to the resulting slurry. After stirring for 2 hours at room temperature, the slurry was filtered. The cake was washed with heptane (3×100 mL) and air-dried to give 80.0 g of 1D. Another 30.2 g of product was recovered from the mother liquor affording a total yield of 95%. $^1$H NMR (CDCl$_3$) d 7.88 (s, 1H), 7.60 (d, J=8.4 Hz, 1H), 7.41 (s, 1H), 6.41 (dd, J=8.4, 2.1 Hz, 1H), 3.34 (d, J=2.1 Hz, 1H), 3.98 (bs, 2H), 3.94 (s, 3H).

1. N-(4-Fluorophenyl)-N2-[3-methoxy-4-(5-oxazolyl)phenyl]glycinamide

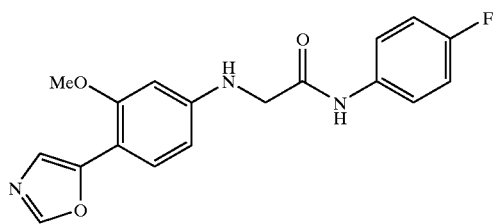

A solution of 1D, (101 mg, 0.53 mmol) and 2-chloro-4'-fluoroacetanilide (50 mg, 0.27 mmol) in DMF (0.15 mL) was heated at 100° C. for 15 h. After the reaction had cooled, the solvent was removed under reduced pressure, and the residue was subjected to preparative HPLC to give 1 as a tan solid. LC/MS: ret. time$^A$32 3.527 min., MS (M+H)$^+$=342.

EXAMPLE 2

N-[3-Methoxy-4-(5-oxazolyl)phenyl]-N2-phenylglycinamide

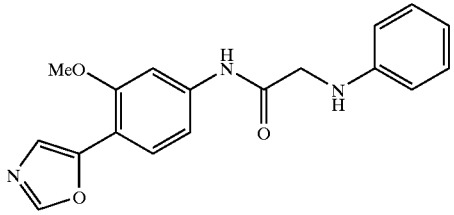

2A. Preparation of 2-Chloro-N-[3-Methoxy-4-(5-oxazolyl)phenyl]-acetamide

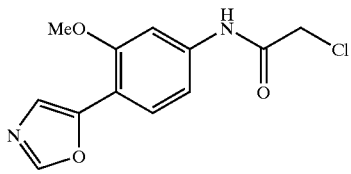

To a solution of 1D (500 mg, 2.63 mmol) and triethylamine (370 μL, 2.89 mmol) in dichloromethane (13.0 mL), was added chloroacetyl chloride (0.23 mL, 2.89 mmol) at 0° C. The reaction mixture was stirred at 0° C. for 10 min. and then at RT for 4 h. The mixture as diluted with dichloromathane, washed with water, brine, and dried over $Na_2SO_4$. The mixture was filtered through celite and concentrated in vacuo to give 2A as a yellow solid. LC/MS: ret. time$^A$=3.123 min., MS (M+H)$^+$=267.

2. Preparation of N-[3-Methoxy-4-(5-oxazolyl)phenyl]-N2-phenylglycinamide

A solution of 2A (30.0 mg, 0.11 mmol) and aniline (30 μL, 0.33 mmol) in DMF (0.1 mL) was heated at 100° C. for 2.5 h. After the reaction had cooled, the solvent was removed under reduced pressure, and the residue was subjected to preparative HPLC to give 2 as a yellow solid. LCIMS: ret. time$^A$=3.576 min., MS (M+H)$^+$=324.

EXAMPLE 3

N-[3-Methoxy-4-(5-oxazolyl)phenyl]-N2-(3-methylphenyl)glycinamide

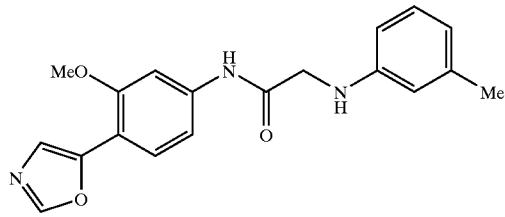

Compound 3 was prepared by a route analogous to that used for the preparation of 2, replacing aniline with m-toluidine. LC/MS: ret. time$^A$=3.759 min., MS (M+H)$^+$=338.

EXAMPLE 4

[[3-Methoxy-4-(5-oxazolyl)phenyl]amino]oxoacetic Acid Ethyl Ester

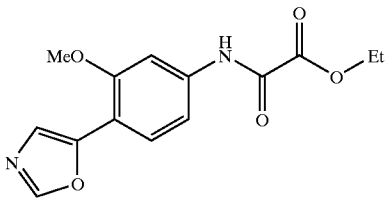

To a solution of 1D (1.0 g, 5.26 mmol) and triethylamine (806 μL, 5.78 mmol) in dichloromethane (26.3 mL), was added ethyl oxalyl chloride (0.646 μL, 5.78 mmol) at 0° C. The reaction mixture was stirred at 0° C. for 10 min. and then at RT for 15 h. The mixture was diluted with dichloromethane, washed with water, brine, and dried over Na$_2$SO$_4$. Following evaporative removal of the solvent, the residue was chromtographed on silica gel, eluting with 80:1 CH$_2$Cl$_2$:MeOH to give 4 as a yellow solid. LCIMS: ret. time$^A$=3.283 min., MS (M+H)$^+$=291.

EXAMPLE 5

N-[3-Methoxy-4-(5-oxazolyl)phenyl]-N'-phenylethanediamide

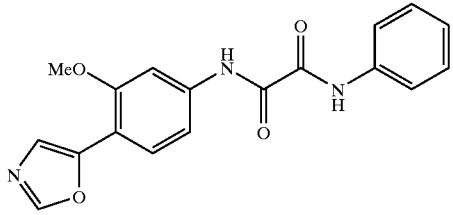

5A. Preparation of [[3-Methoxy-4-(5-oxazolyl)phenyl]amino]oxoacetic Acid

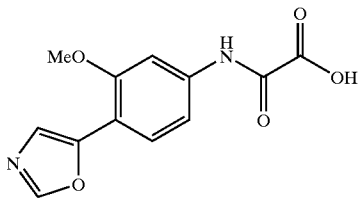

To a solution of 4 (1.45 g, 4.98 mmol) in EtOH (75.0 mL) was added 1N NaOH (12.4 mL, 12.45 mmol) at RT. After stirring for 15 h, the reaction mixture was neutralized with 1N HCl (12.4 mL, 12.45 mmol) and then concentrated to give 5A and NaCl. LC/MS: ret. time$^A$=2.661 min., MS (M+H)$^+$=263.

5B. Preparation of N-[3-Methoxy-4-(5-oxazolyl)phenyl]-N'-phenylethanediamide

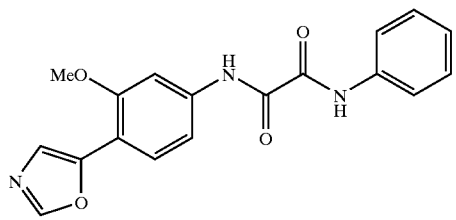

A mixture of the crude product of 5A (47 mg, 0.114 mmol), aniline (10.6 mg, 0.114 mmol), BOP (72.5 mg, 0.172 mmol), and NMM (58 mg, 0.57 mmol) in DMF (0.95 mL) was stirred at RT for 15 h. The mixture was diluted with ethyl acetate, washed with water, brine, and dried over Na$_2$SO$_4$. Following evaporative removal of the solvent, the residue was triturated with MeOH to give 5 as a yellow solid LC/MS: time$^A$=3.960 min., MS (M+H)$^+$=338.

EXAMPLES 6 THROUGH 54

Compounds 6–54 were prepared from the product of 5A by a route analogous hat used for the preparation of 5, replacing aniline with the required HN$_2$-G$^1$. The pounds of these examples have the structures shown in Table 1:

TABLE 1

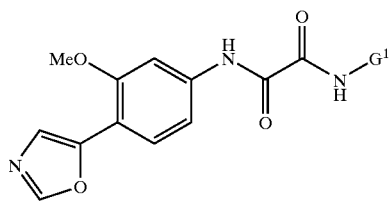

| Ex. No | —G$^1$ | Compound name | HPLC Ret Time$^A$ (min) | MS (M + H)$^+$ |
|---|---|---|---|---|
| 6 | Me-phenyl | N-[3-Methoxy-4-(5-oxazolyl)phenyl]-N'-(2-methylphenyl)ethanediamide | 4.076 | 352 |

TABLE 1-continued

| Ex. No | —G¹ | Compound name | HPLC Ret Time^A (min) | MS (M + H)⁺ |
|---|---|---|---|---|
| 7 | 3-methylphenyl | N-[3-Methoxy-4-(5-oxazolyl)phenyl]-N'-(3-methylphenyl)ethanediamide | 4.162 | 352 |
| 8 | 4-methylphenyl | N-[3-Methoxy-4-(5-oxazolyl)phenyl]-N'-(4-methylphenyl)ethanediamide | 4.181 | 352 |
| 9 | 3-[[[(tetrahydro-3-furanyloxy)carbonyl]amino]methyl]phenyl | (S)-[[3-[[[[3-Methoxy-4-(5-oxazolyl)phenyl]amino]oxoacetyl]-amino]phenyl]methyl]carbamic acid tetrahydro-3-furanyl ester | 3.722 | 481 |
| 10 | 3-methoxyphenyl | N-[3-Methoxy-4-(5-oxazolyl)phenyl]-N'-(3-methoxyphenyl)ethanediamide | 4.141 | 368 |
| 11 | phenylmethyl | N-[3-Methoxy-4-(5-oxazolyl)phenyl]-N'-(phenylmethyl)ethanediamide | 3.948 | 352 |
| 12 | 4-cyanophenyl | N-(4-Cyanophenyl)-N'-[3-methoxy-4-(5-oxazolyl)phenyl]ethanediamide | 3.843 | 363 |
| 13 | 1,1-dimethylethyl | N-(1,1-Dimethylethyl)-N'-[3-methoxy-4-(5-oxazolyl)phenyl]ethanediamide | 4.07 | 318 |
| 14 | 1,1-bis(hydroxymethyl)propyl | N-[1,1-Bis(hydroxymethyl)propyl]-N'-[3-methoxy-4-(5-oxazolyl)phenyl]ethanediamide | 3.34 | 364 |

TABLE 1-continued

| Ex. No | —G¹ | Compound name | HPLC Ret Time[A] (min) | MS (M + H)⁺ |
|---|---|---|---|---|
| 15 | (2-hydroxy-1,1-dimethylethyl) | N-(2-Hydroxy-1,1-dimethylethyl)-N'-[3-methoxy-4-(5-oxazolyl)phenyl]ethanediamide | 3.51 | 334 |
| 16 | | N-[[[3-Methoxy-4-(5-oxazolyl)phenyl]amino]oxoacetyl]-2-methylalanine 1,1-dimethylethyl ester | 4.52 | 404 |
| 17 | | N-(2-Hydroxy-1,1-dimethylpentyl)-N'-[3-methoxy-4-(5-oxazolyl)phenyl]ethanediamide | 4.35 | 376 |
| 18 | | N-[2-[(2-Hydroxy-1,1-dimethylethyl)amino]-1,1-dimethylethyl]-N'-[3-methoxy-4-(5-oxazolyl)phenyl]ethanediamide | 2.88 | 405 |
| 19 | | N-[2-(Dimethylamino)-1,1-dimethylethyl]-N'-[3-methoxy-4-(5-oxazolyl)phenyl]ethanediamide | 2.75 | 361 |
| 20 | | N-(1,1-Diethyl-2-propynyl)-N'-[3-methoxy-4-(5-oxazolyl)phenyl]ethanediamide | 4.45 | 356 |
| 21 | | N-[3-Methoxy-4-(5-oxazolyl)phenyl]-N'-(1,1,3,3-tetramethylbutyl)ethanediamide | 4.25 | 374 |
| 22 | | N-(1,1-Dimethylpropyl)-N'-[3-methoxy-4-(5-oxazolyl)phenyl]ethanediamide | 4.47 | 332 |
| 23 | | N-[1-(Hydroxymethyl)cyclopentyl]-N'-[3-methoxy-4-(5-oxazolyl)phenyl]ethanediamide | 3.94 | 360 |

TABLE 1-continued

| Ex. No | —G¹ | Compound name | HPLC Ret Time^A (min) | MS (M + H)⁺ |
|---|---|---|---|---|
| 24 | (4-fluorobenzyl-tert-butyl group) | N-[2-(4-Fluorophenyl)-1,1-dimethylethyl]-N'-[3-methoxy-4-(5-oxazolyl)phenyl]ethanediamide | 4.82 | 412 |
| 25 | (α-methyl-4-hydroxybenzyl methyl ester group) | N-[[[3-Methoxy-4-(5-oxazolyl)phenyl]amino]oxoacetyl]-α-methyltyrosine methyl ester | 3.98 | 454 |
| 26 | (α-methyl-indolylmethyl methyl ester group) | N-[[[3-Methoxy-4-(5-oxazolyl)phenyl]amino]oxoacetyl]-α-methyltryptophan methyl ester | 4.37 | 477 |
| 27 | (1,1-bis(hydroxymethyl)ethyl group) | N-[1,1-Bis(hydroxymethyl)ethyl]-N'-[3-methoxy-4-(5-oxazolyl)phenyl]-N-methylethanediamide | 3.02 | 350 |
| 28 | (1,1-dimethyl-3-oxobutyl group) | N-[1,1-Dimethyl-3-oxobutyl)-N'-[3-methoxy-4-(5-oxazolyl)phenyl]ethanediamide | 3.74 | 360 |
| 29 | (1-methyl-1-phenylethyl group) | N-[3-Methoxy-4-(5-oxazolyl)phenyl]-N'-(1-methyl-1-phenylethyl)ethanediamide | 4.48 | 380 |
| 30 | (2-hydroxy-1,2-dimethyl-1-phenylpropyl group) | N-(2-Hydroxy-1,2-dimethyl-1-phenylpropyl)-N'-[3-methoxy-4-(5-oxazolyl)phenyl]ethanediamide | 4.29 | 424 |

TABLE 1-continued

| Ex. No | —G¹ | Compound name | HPLC Ret Time^A (min) | MS (M + H)+ |
|---|---|---|---|---|
| 31 | | N-[[[3-Methoxy-4-(5-oxazolyl)phenyl]amino]oxoacetyl]-2-methylalanine methyl ester | 3.68 | 362 |
| 32 | | 1-[[[[3-Methoxy-4-(5-oxazolyl)phenyl]amino]oxoacetyl]-amino]cyclopropanecarboxylic acid methyl ester | 2.63 | 360 |
| 33 | | N-(1-Ethynylcyclohexyl)-N'-[3-methoxy-4-(5-oxazolyl)phenyl]ethanediamide | 3.55 | 368 |
| 34 | | (R)-N-[1-(Hydroxymethyl)-1-methylpropyl]-N'-[3-methoxy-4-(5-oxazolyl)phenyl]-N-methylethanediamide | 2.95 | 348 |
| 35 | | N-[[[3-Methoxy-4-(5-oxazolyl)phenyl]amino]oxoacetyl]-2-methylalanine | 2.60 | 348 |
| 36 | | N-[1,1-Dimethyl-2-oxo-2-(1-piperidinyl)ethyl]-N'-[3-methoxy-4-(5-oxazolyl)phenyl]ethanediamide | 2.87 | 415 |
| 37 | | N-[1,1-Dimethyl-2-(4-methyl-1-piperazinyl)-2-oxoethyl]-N'-[3-methoxy-4-(5-oxazolyl)phenyl]ethanediamide | 2.06 | 430 |

TABLE 1-continued

| Ex. No | —G¹ | Compound name | HPLC Ret Time^A (min) | MS (M + H)⁺ |
|---|---|---|---|---|
| 38 | | N-[1,1-Dimethyl-2-(4-morpholinyl)-2-oxoethyl]-N'-[3-methoxy-4-(5-oxazolyl)phenyl]ethanediamide | 2.41 | 417 |
| 39 | | 4-[2-[[[[3-Methoxy-4-(5-oxazolyl)phenyl]amino]oxoacetyl]amino]-2-methyl-1-oxopropyl]-1-piperazinecarboxylic acid ethyl ester | 2.73 | 488 |
| 40 | | N-[2-[3-(Acetylmethylamino)-1-pyrrolidinyl]-1,1-dimethyl-2-oxoethyl]-N'-[3-methoxy-4-(5-oxazolyl)phenyl]ethanediamide | 2.37 | 472 |
| 41 | | N-[1,1-Dimethyl-2-[methyl[2-(methylamino)ethyl]amino]-2-oxoethyl]-N'-[3-methoxy-4-(5-oxazolyl)phenyl]ethanediamide | 2.05 | 2.057 |
| 42 | | N-[1,1-Dimethyl-2-oxo-2-(propylamino)ethyl]-N'-[3-methoxy-4-(5-oxazolyl)phenyl]ethanediamide | 2.71 | 389 |
| 43 | | N-[1,1-Dimethyl-2-[[2-(methylamino)ethyl]amino]-2-oxoethyl]-N'-[3-methoxy-4-(5-oxazolyl)phenyl]ethanediamide | 2.08 | 404 |

TABLE 1-continued

| Ex. No | —G¹ | Compound name | HPLC Ret Time^A (min) | MS (M + H)⁺ |
|---|---|---|---|---|
| 44 | | N-[1,1-Dimethyl-2-[[2-(4-morpholinyl)ethyl]amino]-2-oxoethyl]-N'-[3-methoxy-4-(5-oxazolyl)phenyl]ethanediamide | 2.14 | 460 |
| 45 | | N-[1,1-Dimethyl-2-oxo-2-[[3-(2-oxo-1-pyrrolidinyl)propyl]amino]ethyl]-N'-[3-methoxy-4-(5-oxazolyl)phenyl]ethanediamide | 2.55 | 472 |
| 46 | | N-[2-[[2-(1H-Imidazol-4-yl)ethyl]amino]-1,1-dimethyl-2-oxoethyl]-N'-[3-methoxy-4-(5-oxazolyl)phenyl]ethanediamide | 2.14 | 441 |
| 47 | | N-[2-[[2-(Acetylamino)ethyl]amino]-1,1-dimethyl-2-oxoethyl]-N'-[3-methoxy-4-(5-oxazolyl)phenyl]ethanediamide | 3.09 | 3.09 |
| 48 | | N-[2-[[2-(1H-Imidazol-1-yl)ethyl]amino]-1,1-dimethyl-2-oxoethyl]-N'-[3-methoxy-4-(5-oxazolyl)phenyl]ethanediamide | 2.14 | 441 |

TABLE 1-continued

| Ex. No | —G¹ | Compound name | HPLC Ret Time[A] (min) | MS (M + H)+ |
|---|---|---|---|---|
| 49 | | N-[1,1-Dimethyl-2-oxo-2-[[2-(4-pyridinyl)ethyl]amino]ethyl]-N'-[3-methoxy-4-(5-oxazolyl)phenyl]ethanediamide | 2.16 | 452 |
| 50 | | N-[1,1-Dimethyl-2-oxo-2-[[(tetrahydro-2-furanyl)methyl]amino]ethyl]-N'-[3-methoxy-4-(5-oxazolyl)phenyl]ethanediamide | 2.63 | 431 |
| 51 | | N-[2-[(2-Methoxyethyl)amino]-1,1-dimethyl-2-oxoethyl]-N'-[3-methoxy-4-(5-oxazolyl)phenyl]ethanediamide | 2.47 | 405 |
| 52 | | N-[2-(Dimethylamino)-1,1-dimethyl-2-oxoethyl]-N'-[3-methoxy-4-(5-oxazolyl)phenyl]ethanediamide | 1.25 | 375 |
| 53 | | N-[2-[4-(2-Methoxyethyl)-1-piperazinyl]-1,1-dimethyl-2-oxoethyl]-N'-[3-methoxy-4-(5-oxazolyl)phenyl]ethanediamide | 1.22 | 474 |

TABLE 1-continued

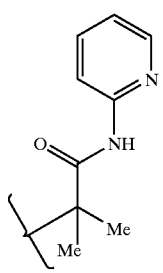

| Ex. No | —G¹ | Compound name | HPLC Ret Time$^A$ (min) | MS (M + H)$^+$ |
|---|---|---|---|---|
| 54 | 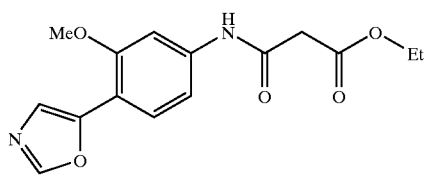 | N-[1,1-Dimethyl-2-oxo-2-(2-pyridinylamino)ethyl]-N'-[3-methoxy-4-(5-oxazolyl)phenyl]ethanediamide | 1.217 | 1.217 |

EXAMPLE 55

3-[[3-Methoxy-4-(5-oxazolyl)phenyl]amino]-3-oxopropanoic Acid Ethyl Ester

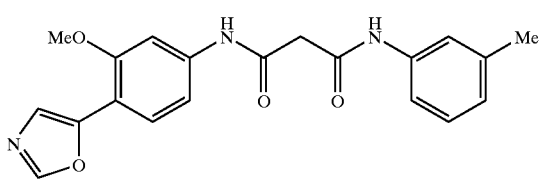

55 was prepared from 1D by a route analogous to that used for the preparation of 4, replacing ethyl oxalyl chloride with ethyl malonyl chloride. LCJMS: ret. time$^A$=69 min., MS (M+H)$^+$=305.

EXAMPLE 56

N-[3-Methoxy-4-(5-oxazolyl)phenyl]-N'-(3-methylphenyl)propanediamide

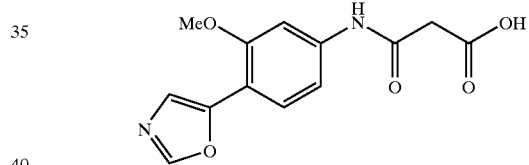

56 A. Preparation of 3-[[3-Methoxy-4-(5-oxazolyl)phenyl]amino]-3-oxopropanoic acid 56 A was prepared from 55 by a route analogous to that used for the preparation of 5A. LC/MS: ret. time$^A$=2.611 min., MS (M+H)$^+$=277.

56B. Preparation of N-[3-Methoxy-4-(5-oxazolyl)phenyl]-N'-(3-methylphenyl) propanediamide 56 was prepared from 56A by a route analogous to that used for the preparation of 5, replacing aniline with m-toluidine. LC/MS: ret. time$^A$=3.783 min., MS (M+H)$^+$=366.

EXAMPLES 57 AND 58

Compounds 57 and 58 were prepared from 56A, by a route analogous to that used for the preparation of 5, replacing, aniline with the required HN$_2$-G$^2$. 57 and 58 have the structures as shown below and in Table 2:

TABLE 2

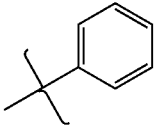

| Ex. No | —G² | Compound name | HPLC Ret Time$^A$ (min) | MS (M + H)⁺ |
|---|---|---|---|---|
| 57 | 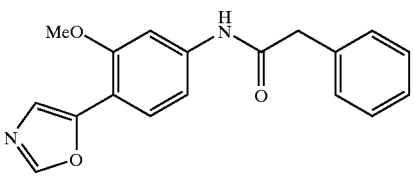 | N-[3-Methoxy-4-(5-oxazolyl)phenyl]-N'-(phenyl)propanediamide | 3.562 | 352 |
| 58 | 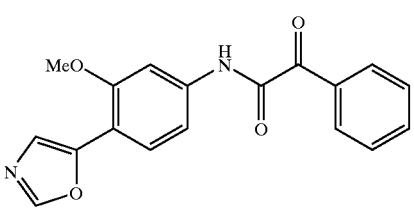 | (S)-[[3-[[3-[[3-Methoxy-4-(5-oxazolyl)phenyl]amino]-1,3-dioxopropyl]amino]-phenyl]methyl]carbamic acid tetrahydro-3-furanyl ester | 3.335 | 495 |

EXAMPLE 59

N-[3-Methoxy-4-(5-oxazolyl)phenyl] benzeneacetamide

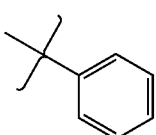

Compound 59 was prepared from 1D by a route analogous to that used for the preparation of 4, replacing ethyl oxalyl chloride with phenylacetic acid. LC/MS: ret. time$^A$= 3.617 min., MS (M+H)⁺=309.

EXAMPLE 60

N-[3-Methoxy-4-(5-oxazolyl)phenyl]-α-oxobenzeneacetamide

Compound 60 was prepared from the product of 1D by a route analogous to that used for the preparation of 4, replacing ethyl oxalyl chloride with benzoylformic acid. LC/MS: ret. time$^A$=3.843 min., MS (M+H)⁺=323.

EXAMPLE 61

N-[3-Methoxy-4-(5-oxazolyl)phenyl]-1H-indole-2-carboxamide

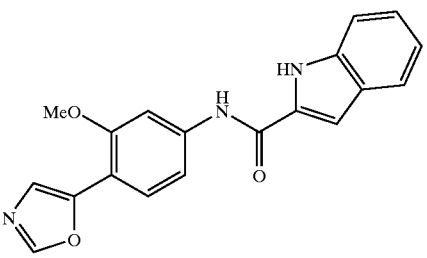

To a solution of 1D (0.5 g, 2.63 mmol) was sequentially added anhydrous dimethylformarnide (8 mL), indole-2-carboxylic acid (0.42 g, 2.63 mmol) and 1-(3-dimethylaminopropyl)-3-ethylcarbodiimide (0.5 g, 2.63 mmol). The reaction mixture was stirred for 18 hours at room temperature, concentrated under reduced pressure and partitioned between ethyl acetate (50 mL) and 1N HCl (20 mL). The ethyl acetate layer is successively washed with 1N NaOH (20 mL), brine (20 mL), dried over sodium sulfate and concentrated to yield 61 (0.36 g, 41%). LC/MS ret. time$^A$=4.330 min.; MS (M+H)⁺=334.

EXAMPLE 62

N-[3-Methoxy-4-(5-oxazolyl)phenyl]-1-methyl-1H-indole-2-carboxamide

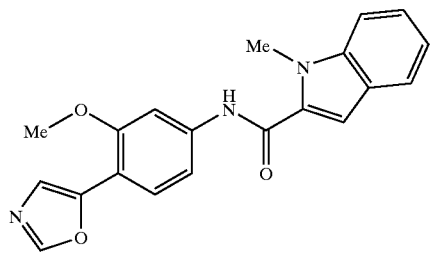

To a solution of 1D (30 mg, 0.158 mmol) was sequentially added 1-Methylindole-2-carboxylic acid (28 mg, 0.158 mmol), BOP (100 mg, 0.237 mmol), NMM (80 mg, 0.790 mmol) and anhydrous dimethylformamide (1.3 mL). The reaction mixture was stirred for 18 hours at room temperature, concentrated under reduced pressure and purified by preparative HPLC to yield 32 mg of 62. LC/MS ret time$^A$=4.177 min.; MS (M+H)$^+$=348.

EXAMPLES 63–65

Compounds 63–65 were prepared from the product of 1D by a route analogous to that used for the preparation of 62, replacing 1-Methylindole-2-carboxylic acid with the required HO(CO)—G$^3$. The compounds of these examples have the structures shown in Table 3:

TABLE 3

| Ex. No | —G$^3$ | Compound name | HPLC Ret time$^B$ (min) | MS (M + H)$^+$ |
|---|---|---|---|---|
| 63 | (benzofuran-2-yl) | N-[3-Methoxy-4-(5-oxazolyl)phenyl]-2-benzofurancarboxamide | 4.023 | 335 |
| 64 | (benzo[b]thiophen-2-yl) | N-[3-Methoxy-4-(5-oxazolyl)phenyl]benzo[b]thiophene-2-carboxamide | 4.167 | 351 |
| 65 | (1,3-benzodioxol-5-yl) | N-[3-Methoxy-4-(5-oxazolyl)phenyl]-1,3-benzodioxole-5-carboxamide | 3.687 | 339 |

EXAMPLE 66

N-[3-Methoxy-4-(5-oxazolyl)phenyl]-1-methyl-1H-pyrrole-2-carboxamide

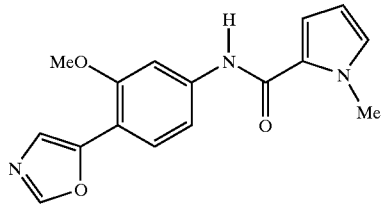

To a mixture of 3-methoxy-4-(5-oxazoyl)aniline 1D (0.050 g, 0.263 mmol) and 1-methyl-2-pyrolecarboxylic acid (0.033 g, 0.263 mmol) in 1.0 mL of dimethylformamide (0.050 g, 0.263 mmol) in a 2 dram rubber-lined screwcap vial was added 1-ethyl-3-(3-dimetliylaminopropyl)-carbodiimide-HCl. The reaction mixture was placed in a lnnova 2000 Platformn Shaker equipped with a standard heat block and shaken at 200 rpm overnight at approximately 50° C. Aqueous acid (10%, 1 mL) was added, and the mixture was extracted three times with ethyl acetate. The organic layer was washed with a 1N solution of sodium hydroxide, washed with brine, and dried over anhydrous sodium sulfate. Concentration under reduced pressure afforded 66 as a pale yellow solid. The product was 96% pure by analytical HPLC with a ret. time=3.53 min. (Column: YMC S5 ODS 4.6×50 mm Ballistic; Solvent A=10% MeOH, 90% $H_2O$, 0.2% $H_3PO_4$; Solvent B=90% MeOH, 10% $H_2O$, 0.2% $H_3PO_4$) and a LC/MS $(M+H)^-$=298.23.

EXAMPLE 67

5-(1,1-Dimethylethyl)-N-[3-methoxy-4-(5-oxazolyl)phenyl]-2-furancarboxamide

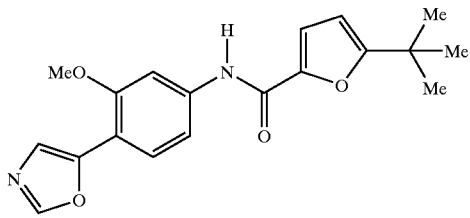

A mixture of 3-methoxy-4-(5-oxazoyl)aniline 1D (0.050 g, 0.263 mmol), 5-tert-butyl-2-furoic acid (0.044 g, 0.263 mmol), and 1-ethyl-3-(3-dimethylaminopropyl)-carbodiimide-HCl (0.050 g, 0.263 mmol) in 1.0 mL of dimethylformamide was subjected to the procedure used for the preparation of 66 to give 52.1 mg of 67 as a yellow solid. The product, 67, was 95% pure by analytical HPLC with a retention time=3.82 min. (Column: YMC S5 ODS 4.6×50 mm Ballistic; Solvent A=10% MeOH, 90% $H_2O$, 0.2% $H_3PO_4$; Solvent B=90% MeOH, 10% $H_2O$, 0.2% $H_3PO_4$) and a LC/MS $(M+H)^+$=341.19.

EXAMPLE 68

N-[3-Methoxy-4-(5-oxazolyl)phenyl]-4,5-dimethyl-2-furancarboxamide

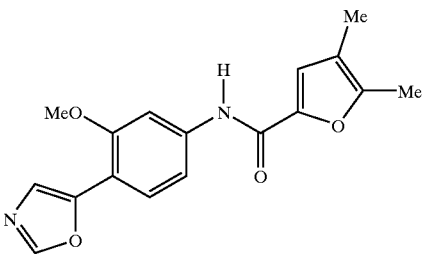

A mixture of 3-methoxy-4-(5-oxazoyl)aniline 1D (0.050 g, 0.263 mmol), 2,3-dimethylfuran-5-carboxylic acid (0.037 g, 0.263 mmol), and 1-ethyl-3-(3-dimethylaminopropyl)-carbodiimide-HCl (0.050 g, 0.263 mmol) in 1.0 mL of dimethylformamide was subjected to the procedure used for the preparation of 66 to give 23.0 mg of 68 as a pale yellow solid. The product, 68, was 95% pure by analytical HPLC with a retention time=3.79 min. (Column: YMC S5 ODS 4.6×50 mm Ballistic; Solvent A=10%, MeOH, 90% $H_2O$, 0.2% $H_3PO_4$; Solvent B=90% MeOH, 10% $H_2O$, 0.2% $H_3PO_4$) and a LC/MS $(M+H)^+$=319.29.

EXAMPLE 69

N-[3-Methoxy-4-(5-oxazolyl)phenyl]-5-methyl-2-thiophenecarboxamide

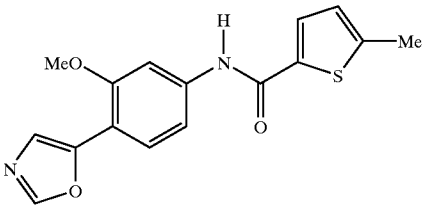

A mixture of 3-methoxy-4-(5-oxazoyl)aniline 1D (0.050 g, 0.263 mmol), 5-methyl-2-thiophenecarboxylic acid (0.037 g, 0.263 mmol), and 1-ethyl-3-(3-dimethylaminopropyl)-carbodiimide-HCl (0.050 g, 0.263 mmol) in 1.0 mL of dimethylformamide was subjected to the procedure used for the preparation of 66 to give 25.8 mg of 69 as a yellow solid. The product, 69, was 92% pure by analytical HPLC with a retention time=3.77 min. (Column: YMC S5 ODS 4.6×50 mm Ballistic; Solvent A=10% MeOH, 90% $H_2O$, 0.2% $H_3PO_4$; Solvent B=90% MeOH, 10% $H_2O$, 0.2% $H_3PO_4$) and a LC/MS $(M+H)^+$=315.17.

EXAMPLE 70

N-[3-Methoxy-4-(5-oxazolyl)phenyl]-5-(2-pyridinyl)-2-thiophenecarboxamide

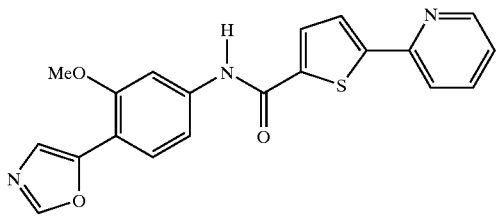

A mixture of 3-methoxy-4-(5-oxazoyl)aniline 1D (0.050 g, 0.263 mmol), 5-(pyrid-2-yl)-thiophene-2-carboxylic acid (0.054 g, 0.263 mmol), and 1-ethyl-3-(3-dimethylaminopropyl)-carbodiimide-HCl (0.050 g, 0.263 mmol) in 1.0 mL of dimethylformamide was subjected to the procedure used for the preparation of 66 to give 4.6 mg of 70 as a yellow solid. The product, 70, was 80% pure by analytical HPLC with a retention time 3.83 min. (Column: YMC S5 ODS 4.6×50 mm Ballistic; Solvent A=10% MeOH, 90% H$_2$O, 0.2% H$_3$PO$_4$; Solvent B=90% MeOH, 10% H$_2$O, 0.2% H$_3$PO$_4$) and a LC/MS (M+H)$^+$=378.

EXAMPLE 71

N-[3-Methoxy-4-(5-oxazolyl)phenyl]-2,4-dimethyl-5-thiazolecarboxamide

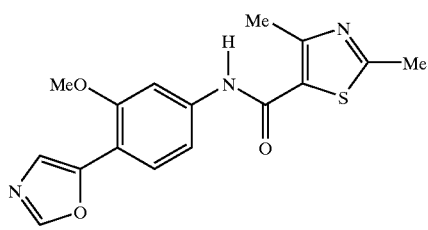

A mixture of 3-methoxy-4-(5-oxazoyl)aniline 1D (0.050 g, 0.263 mmol), 2,4-dimethylthiazole-5-carboxylic acid (0.041 g, 0.263 mmol), and 1-ethyl-3-(3-dimethylaminopropyl)-carbodiimnide-HCl (0.050 g, 0.263 mmol) in 1.0 mL of dimethylformamide was subjected to the procedure used for the preparation of 66 to give 15.0 mg of 71 as a pale yellow solid. The product, 71, was 93% pure by analytical HPLC with a retention time=3.46 min. (Column: YMC S5 ODS 4.6×50 mm Ballistic; Solvent A=10% MeOH, 90% H$_2$O, 0.2% H$_3$PO$_4$; Solvent B=90% MeOH, 10% H$_2$O, 0.2% H$_3$PO$_4$) and a LC/MS (M+H)$^+$=330.16.

EXAMPLE 72

5-Hydroxy-N-[3-methoxy-4-(5-oxazolyl)phenyl]-1H-indole-2-carboxamide

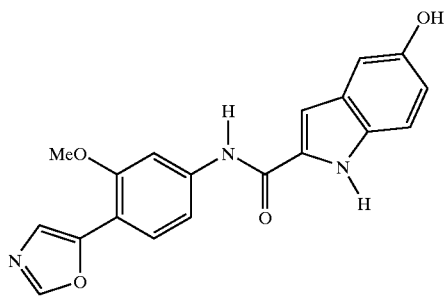

A mixture of 3-methoxy-4-(5-oxazoyl)aniline 1D (0.050 g, 0.263 mmol), 5-hydroxy-2-indolecarboxylic acid (0.047 g, 0.263 mmol), and 1-ethyl-3-(3-dimethylaminopropyl)-carbodiimide-HCl (0.050 g, 0.263 mmol) in 1.0 mL of dimethylformamide was subjected to the procedure used for the preparation of 66 to give a mixture that contained 45% of 72. The mixture was washed with ether (2×) to give 9.2 mg of 72 as a pale yellow solid. The product, 72, was 96% pure by analytical HPLC with a retention time=3.39 min. (Column: YMC S5 ODS 4.6×50 mm Ballistic; Solvent A=10% MeOH, 90% H$_2$O, 0.2% H$_3$PO$_4$; Solvent B=90% MeOH, 10% H$_2$O, 0.2% H$_3$PO$_4$) and a LC/MS (M+H)$^+$=350.20.

EXAMPLE 73

7-Methoxy-N[3-methoxy-4-(5-oxazolyl)phenyl]-2-benzofurancarboxamide

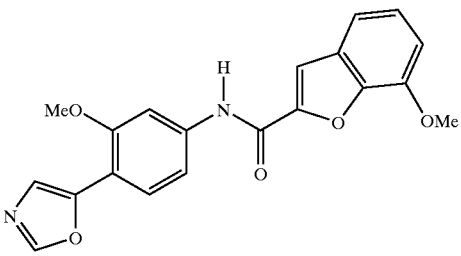

A mixture of 3-methoxy-4-(5-oxazoyl)aniline 1D (0.100 g, 0.526 mmol), 7-methoxy-2-benzofurancarboxylic acid (0.101 g, 0.526 mmol), and 1-ethyl-3-(3-dimethylaminopropyl)-carbodiimide-HCl (0.101 g, 0.526 mmol) in 1.5 mL of dimethylformamide was subjected to the procedure used for the preparation of 66 to give a crude product which was washed with ether (2×) to give 78.0 mg of 73 as a pale yellow solid. The product, 73, was 99% pure by analytical HPLC with a retention time=4.15 min. (Column: YMC S5 ODS 4.6×50 mm Ballistic; Solvent A=10% MeOH, 90% H$_2$O, 0.2% H$_3$PO$_4$; Solvent B=90% MeOH, 10% H$_2$O, 0.2% H$_3$PO$_4$) and a LC/MS (M+H)$^+$=365.20.

EXAMPLE 74

8-Hydroxy-N-[3-methoxy-4-(5-oxazolyl)phenyl]-2-quinolinecarboxamide

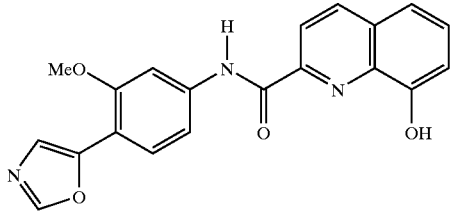

A mixture of 3-methoxy-4-(5-oxazoyl)aniline 1D (0.050 g, 0.263 mmol), 8-hydroxyquinoline-2-carboxylic acid (0.050 g, 0.263 mmol), and 1-ethyl-3-(3-dimethylaminopropyl)-carbodiimide-HCl (0.050 g, 0.263 mmol) in 1.0 mL of dimethylformamide was subjected to the procedure used for the preparation of 66 to give 23.0 mg of 74 as a pale yellow solid. The product, 74, was 93% pure by analytical HPLC with a retention time=4.22 min. (Column: YMC S5 ODS 4.6×50 mm Ballistic; Solvent A=10% MeOH, 90% $H_2O$, 0.2% $H_3PO_4$; Solvent B=90% MeOH, 10% $H_2O$, 0.2% $H_3PO_4$) and a LC/MS $(M+H)^+$=362.26.

EXAMPLE 75
(E)-N-[3-Methoxy-4-(5-oxazolyl)phenyl]-3-phenyl-2-propenamide

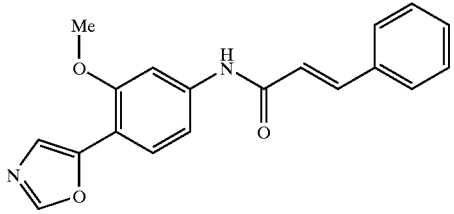

A mixture of 3-methoxy-4-(5-oxazolyl)aniline 1D (15.0 mg, 0.0789 mmol), trans-cinnamic acid (17.5 mg, 0.118 mmol), 1-ethyl-3-(3-dimethylaminopropyl)carbodiimide hydrochloride (18.2 mg, 0.949 mmol), 4-dimethylamino pyridine (9.6 mg, 0.786 mmol), in dichloromethane (2 mL) and DMF (0.5 mL) was shaken in a 16×100 mm test tube for 24 h. The reaction solution was diluted with dichloromethane (4 mL), and washed successively with 1N NaOH (1 mL) and 1N HCl (1 mL). Evaporation of solvent provided the desired product 75 (18.2 mg, 72% yield). Ret. Time: 4.25 min LC/MS conditions: Column: Shimadzu 4.6×50 mm Ballistic. Solvent A=10% MeOH, 90% $H_2O$, 0.1% TFA. Solvent B=90% MeOH, 10% $H_2O$, 0.1% TFA and a LC/MS $(M+H)^+$=321.

EXAMPLES 76–99

Compound 76 through 99 were prepared from the product 1D by a route analogous to that used for the preparation of 75, replacing trans-cinnamic acid with the required HO(CO)—$G^4$.

If the products carry acetic or basic moieties, the solvent was evaporated under vacuum and products were purified by preparative HPLC. The compounds of these examples have the structures shown in Table 4:

TABLE 4

| Ex. No | —$G^4$ | Compound name | HPLC Ret Time[B] (min) | MS $(M + H)^+$ |
|---|---|---|---|---|
| 76 |  | N-[3-Methoxy-4-(5-oxazolyl)phenyl]benzamide | 3.77 | 295 |
| 77 |  | (E)-N-[3-Methoxy-4-(5-oxazolyl)phenyl]-3-(2-methylphenyl)-2-propenamide | 4.17 | 335 |

TABLE 4-continued

| Ex. No | —G⁴ | Compound name | HPLC Ret Time[B] (min) | MS (M + H)⁺ |
|---|---|---|---|---|
| 78 | 4-methylphenyl vinyl | (E)-N-[3-Methoxy-4-(5-oxazolyl)phenyl]-3-(4-methylphenyl)-2-propenamide | 4.19 | 335 |
| 79 | 2-fluorophenyl vinyl | (E)-3-(2-Fluorophenyl)-N-[3-methoxy-4-(5-oxazolyl)phenyl]-2-propenamide | 4.06 | 339 |
| 80 | 3-fluorophenyl vinyl | (E)-3-(3-Fluorophenyl)-N-[3-methoxy-4-(5-oxazolyl)phenyl]-2-propenamide | 4.09 | 339 |
| 81 | 4-fluorophenyl vinyl | (E)-3-(4-Fluorophenyl)-N-[3-methoxy-4-(5-oxazolyl)phenyl]-2-propenamide | 4.04 | 339 |
| 82 | 2-chlorophenyl vinyl | (E)-3-(2-Chlorophenyl)-N-[3-methoxy-4-(5-oxazolyl)phenyl]-2-propenamide | 4.21 | 355 |
| 83 | 3-chlorophenyl vinyl | (E)-3-(3-Chlorophenyl)-N-[3-methoxy-4-(5-oxazolyl)phenyl]-2-propenamide | 4.29 | 355 |
| 84 | 4-chlorophenyl vinyl | (E)-3-(4-Chlorophenyl)-N-[3-methoxy-4-(5-oxazolyl)phenyl]-2-propenamide | 4.27 | 355 |

TABLE 4-continued

| Ex. No | —G⁴ | Compound name | HPLC Ret Time^B (min) | MS (M + H)⁺ |
|---|---|---|---|---|
| 85 | | (E)-N-[3-Methoxy-4-(5-oxazolyl)phenyl]-3-[2-(trifluoromethyl)phenyl]-2-propenamide | 4.21 | 389 |
| 86 | | (E)-3-(3-Cyanophenyl)-N-[3-methoxy-4-(5-oxazolyl)phenyl]-2-propenamide | 3.89 | 346 |
| 87 | | (E)-3-[4-(Acetylamino)phenyl]-N-[3-methoxy-4-(5-oxazolyl)phenyl]-2-propenamide | 3.76 | 378 |
| 88 | | (E)-3-(2,3-Dimethoxyphenyl)-N-[3-methoxy-4-(5-oxazolyl)phenyl]-2-propenamide | 3.96 | 381 |
| 89 | | (E)-3-(2,6-Difluorophenyl)-N-[3-methoxy-4-(5-oxazolyl)phenyl]-2-propenamide | 4.11 | 357 |
| 90 | | (E)-N-[3-Methoxy-4-(5-oxazolyl)phenyl]-3-(2,3,4-trimethoxyphenyl)-2-propenamide | 3.97 | 411 |
| 91 | | (E)-2-Fluoro-N-[3-methoxy-4-(5-oxazolyl)phenyl]-3-phenyl-2-propenamide | 4.18 | 339 |

TABLE 4-continued

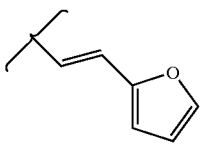

| Ex. No | —G⁴ | Compound name | HPLC Ret Time[B] (min) | MS (M + H)⁺ |
|---|---|---|---|---|
| 92 | 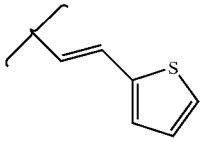 | (E)-3-(2-Furanyl)-N-[3-methoxy-4-(5-oxazolyl)phenyl]-2-propenamide | 3.73 | 311 |
| 93 | 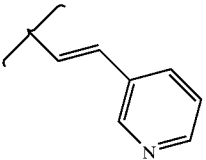 | (E)-N-[3-Methoxy-4-(5-oxazolyl)phenyl]-3-(2-thienyl)-2-propenamide | 3.90 | 327 |
| 94 | 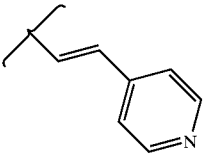 | (E)-N-[3-Methoxy-4-(5-oxazolyl)phenyl]-3-(3-pyridinyl)-2-propenamide | 2.84 | 322 |
| 95 | 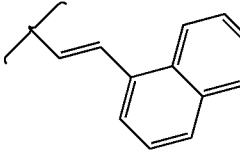 | (E)-N-[3-Methoxy-4-(5-oxazolyl)phenyl]-3-(4-pyridinyl)-2-propenamide | 2.81 | 322 |
| 96 | 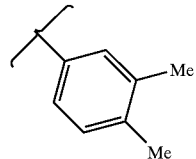 | (E)-N-[3-Methoxy-4-(5-oxazolyl)phenyl]-3-(1-naphthalenyl)-2-propenamide | 4.38 | 371 |
| 97 |  | N-[3-Methoxy-4-(5-oxazolyl)phenyl]-3,4-dimethylbenzamide | 4.04 | 334 |
| 98 | 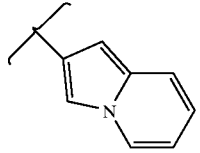 | N-[3-Methoxy-4-(5-oxazolyl)phenyl]-2-indolizinecarboxamide | 3.78 | 334 |

TABLE 4-continued

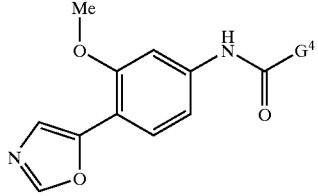

| Ex. No | —G⁴ | Compound name | HPLC Ret Time$^B$ (min) | MS (M + H)⁺ |
|---|---|---|---|---|
| 99 | | (E)-N-[3-Methoxy-4-(5-oxazolyl)phenyl]-3-[3-methoxy-4-(phenylmethoxy)phenyl]-2-propenamide | 4.40 | 457 |

The materials required for the synthesis of the compounds described above are commercially available. The compound below (of Example 100) is useful as an intermediate in the preparation of 9 ad 58.

EXAMPLE 100

3-Aminophenyl)-(+)-tetrahydrofuranylcarbamate

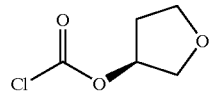

100A Preparation of 3-Aminobenzylamine

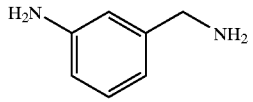

3-Cyanoanline (0.50 g, 4.23 mmol) in 100 mL of MeOH wa; stirred overnight at room temperature under a $H_2$ environment in the presence of 10% Pd/C (100 mg). The Pd/C was removed by filtration trough a pad of Celilte, and the resulting filtrate was concentrated under reduced pressure to give 0.516 g (~100%) of 100A as a thick oil. The product was used without any further purification.

100B. Preparation of (S)-(+)tetrahydrofuranylchloroformate

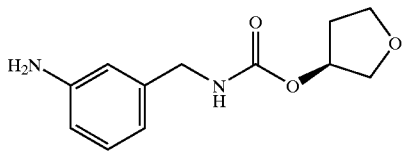

To a solution of phosgene (8 mL of a ~20% in toluene, 17.0 mmol) in 20 mL of dichloromethane at 0° C. was added a solution of (S)-(+)-hydroxytetrahydrofuran (0.50 g, 5.67 mmol) and triethylamine (1.58 mL, 11.3 mmol) in 15 mL of dichloromethane dropwise over 20 min. The reaction mixture was stirred for 15 h at room temperature. The solvent was removed under reduced pressure, and the resulting residue was dissolved in ether. The triethylamine hydrochloride salt was removed by filtration. Concentration followed by purification of the residue by silica gel chromatography afforded 0.509 g (60%) of 100B as a clear oil, 100C. Preparation of 3 aminopheny)-(+)-tetrahydrofuranylcarbamate

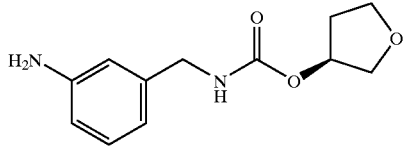

To 100A (0.509 g, 3.38 mmol) in 15 mL of dichloromethane at 0° C. was added a solution of the product of 100B (0.517 g, 4.23 mmol) and triethylamine (0.94 mL, 6.76 mmol) in 15 mL of dichloromethane dropwise over 10 min. The reaction mixture was stirred overnight at room temperature. The solvent was removed under reduced pressure, and the residue was dissolved in ether. The solid triethylamine hydrochloride salt was removed by filtration. Concentration followed by purification of the residue by silica gel chromatography afforded 0.508 g (64%) of 100 as a clear oil. LC/MS: ret. time$^A$=1.07 min.; MS (M+H)⁺=237.

Although the present invention has been described in some detail by way of illustration and example for purposes of clarity and understanding, it will be apparent that certain changes and modifications may be practiced within the scope of the appended claims.

We claim:

1. A compound of the following formula I, or a pharmaceutically acceptable salt thereof:

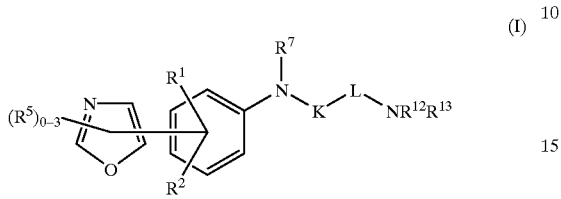

(I)

wherein:

$R^1$ and $R^2$ are each independently selected from the group consisting of H, F, Cl, Br, I, $NO_2$, $CF_3$, CN, $OCF_3$, OH, $C_1$–$C_4$alkoxy-, $C_1$–$C_4$alkylcarbonyl-, $C_1$–$C_6$ alkyl, hydroxy $C_1$–$C_4$ alkyl-, $C_3$–$C_6$ alkenyl, $C_3$–$C_6$ alkynyl, $C_3$–$C_{10}$ cycloalkyl($C_0$–$C_4$alkyl)-, $H_2N(C_0$–$C_4)$alkyl-, $R^6$ HN($C_0$–$C_4$)alkyl-, $R^6R^7N(C_0$–$C_4)$alkyl-, $R^7S$ ($C_0$–$C_4$)alkyl-, $R^7S(O)$ ($C_0$–$C_4$)alkyl-, $R^7SO_2(C_0$–$C_4)$ alkyl-, $R^6R^7NSO_2(C_0$–$C_4)$alkyl-, $HSO_3$, $HO_2C(C_0$–$C_4)$ alkyl-, $R^6O_2C(C_0$–$C_4)$alkyl-, and $R^6R^7NCO(C_0$–$C_4)$ alkyl-, or $R^1$ and $R^2$, when on adjacent carbon atoms, and when taken together are methylenedioxy or ethylenedioxy;

$R^5$ is independently selected from H, F, Cl, Br, I, $NO_2$, CN, $CF_3$, $OCF_3$, OH, $C_1$–$C_4$alkoxy-, hydroxy$C_1$–$C_4$ alkyl-, $C_1$–$C_4$ alkylcarbonyl-, $CO_2H$, $CO_2R^6$, $CONR^6R^7$, $NHR^6$, and $NR^6R^7$;

$R^6$ is selected from H, $C_1$–$C_8$ alkyl, $C_3$–$C_6$ alkenyl, $C_3$–$C_6$ alkynyl, $C_3$–$C_{10}$ cycloalkyl($C_0$–$C_4$ alkyl)-, aryl($C_0$–$C_4$ alkyl)-, and heterocyclic ($C_0$–$C_4$ alkyl)-, wherein said aryl or heterocyclic groups are substituted with 0–2 substituents independently selected from $C_1$–$C_4$ alkyl, $C_1$–$C_4$ alkoxy, hydroxy $C_0$–$C_4$ alkyl, oxo, F, Cl, Br, $CF_3$, $NO_2$, CN, $OCF_3$, $NH_2$, $NHR^7$, $NR^7R^8$, $SR^7$, $S(O)R^7$, $SO_2R^7$, $SO_2NR^7R^8$, $CO_2H$, $CO_2R^7$, and $CONR^7R^8$;

$R^7$ and $R^8$ are each independently selected from H, $C_1$–$C_8$ alkyl, $C_3$–$C_6$ alkenyl, $C_3$–$C_6$ alkynyl, $C_3$–$C_{10}$ cycloalkyl($C_0$–$C_4$ alkyl)-, $C_1$–$C_6$ alkylcarbonyl, $C_3$–$C_7$ cycloalkyl($C_0$–$C_5$ alkyl)carbonyl, $C_1$–$C_6$ alkoxycarbonyl, $C_3$–$C_7$ cycloalkyl($C_0$–$C_5$ alkoxy) carbonyl, aryl($C_1$–$C_5$ alkoxy)carbonyl, arylsulfonyl, aryl($C_0$–$C_4$ alkyl)-, heterocyclic($C_1$–$C_5$ alkoxy) carbonyl, heterocyclic sulfonyl and heterocyclic ($C_0$–$C_4$ alkyl)-, wherein said aryl or heterocyclic groups are substituted with 0–2 substituents independently selected from the group consisting of $C_1$–$C_4$ alkyl, $C_1$–$C_4$ alkoxy, F, Cl, Br, $CF_3$, CN, and $NO_2$;

or $R^6$ and $R^7$, or $R^6$ and $R^8$, or $R^7$ and $R^8$, when both substituents are on the same nitrogen atom, do or do not form, with the nitrogen atom to which they are attached, a heterocycle selected from 1-aziridinyl, 1-azetidinyl, 1-piperidinyl, 1-morpholinyl, 1-pyrrolidinyl, thiamorpholinyl, thiazolidinyl, and 1-piperazinyl, said heterocycle is unsubstituted or substituted with 0–3 groups selected from oxo, $C_1$–$C_6$ alkyl, $C_3$–$C_7$ cycloalkyl($C_0$–$C_4$ alkyl)-, $C_1$–$C_6$ alkylcarbonyl, $C_3$–$C_7$ cycloalkyl($C_0$–$C_5$ alkyl) carbonyl, $C_1$–$C_6$ alkoxycarbonyl, $C_3$–$C_7$ cycloalkyl ($C_0$–$C_5$ alkoxy)carbonyl, aryl($C_0$–$C_5$ alkyl), heterocyclic($C_0$–$C_5$ alkyl), aryl($C_1$–$C_5$ alkoxy) carbonyl, heterocyclic($C_1$–$C_5$ alkoxy)carbonyl, $C_1$–$C_6$ alkylsulfonyl, arylsulfonyl, and heterocyclicsulfonyl, wherein said aryl or heterocyclic groups are substituted with 0–2 substituents independently selected from $C_1$–$C_4$ alkyl, $C_1$–$C_4$ alkoxy, F, Cl, Br, $CF_3$, CN, and $NO_2$;

K is selected from —C(=O)— and —$CHR^9$—;

L is selected from —C(=O), —$CHR^9$—, —$CR^{10}R^{11}$—, —$CR^{10}R^{11}$—(C=O), —$HR^{15}C$—$CHR^{16}$—, and —$R^{15}C$=$CR^{16}$;

$R^9$ is selected from H, $C_1$–$C_8$ alkyl, $C_3$–$C_6$ alkenyl, $C_3$–$C_{10}$ cycloalkyl($C_0$–$C_4$ alkyl)-, aryl($C_0$–$C_4$ alkyl)-, and heterocyclic($C_0$–$C_4$ alkyl)-, wherein said aryl or heterocyclic groups are substituted with 0–2 substituents independently selected from $C_1$–$C_4$ alkyl, $C_1$–$C_4$ alkoxy, F, Cl, Br, $CF_3$, and $NO_2$;

$R^{10}$ is selected from H, F, Cl, Br, $C_1$–$C_6$ alkoxy, $C_1$–$C_8$ alkyl, $C_3$–$C_6$ alkenyl, $C_3$–$C_{10}$ cycloalkyl($C_0$–$C_4$ alkyl)-, aryl($C_0$–$C_4$ alkyl)-, and heterocyclic($C_0$–$C_4$ alkyl)-, wherein said aryl or heterocyclic groups are substituted with 0–2 substituents independently selected from $C_1$–$C_4$ alkyl, $C_1$–$C_4$ alkoxy, F, Cl, Br, $CF_3$, CN, and $NO_2$;

$R^{11}$ is selected from H, F, Cl, Br, OMe, $C_1$–$C_8$ alkyl, $C_3$–$C_6$ alkenyl, $C_3$–$C_{10}$ cycloalkyl($C_0$–$C_4$ alkyl)-, aryl ($C_0$–$C_4$ alkyl)-, and heterocyclic($C_0$–$C_4$ alkyl)-, wherein said aryl or heterocyclic groups are substituted with 0–2 substituents independently selected from $C_1$–$C_4$ alkyl, $C_1$–$C_4$ alkoxy, F, Cl, Br, $CF_3$, CN, and $NO_2$;

or $R^{10}$ and $R^{11}$, when on the same carbon atom, do or do not form, with the carbon atoms to which they are attached, a 3–7 membered carbocyclic or 3–7 membered heterocyclic non-aromatic ring system, said carbocyclic or heterocyclic ring is unsubstituted or substituted with 0–2 substituents independently selected from $C_1$–$C_4$ alkyl, $C_1$–$C_4$ alkoxy, hydroxy $C_0$–$C_4$ alkyl, oxo, F, Cl, Br, $CF_3$, and $NO_2$;

$R^{12}$ is selected from $C_1$–$C_8$ alkyl and monocyclic or bicyclic aryl($C_0$–$C_4$ alkyl)-, wherein said aryl groups are substituted with 0–3 substituents independently selected from $R^{14}$; and $R^{13}$ is H;

$R^{14}$ is selected from H, $C_1$–$C_{10}$ alkyl, $NO_2$, $CF_3$, CN, F, Cl, Br, $C_1$–$C_{10}$ alkylcarbonyl, haloalkyl, haloalkoxy, OH, $NR^6R^7(C_0$–$C_4$ alkyl)-, $R^6$ C(=O)O($C_{0-C4}$ alkyl)-, $R^6OC(=O)O$ ($C_0$–$C_4$ alkyl)-, $R^6O(_0$–$C_4$ alkyl), $R^6R^7$ NC(=O)O ($C_0$–$C_4$ alkyl)-, $R^6R^7$ NC(=O) ($C_0$–$C_4$ alkyl)-, $R^6O(CR^{10}R^{11})_{2-6}R^6NC(=O)$ ($C_0$–$C_4$ alkyl)-, $R^6R^7N(CR^{10}R^{11})_{2-6}R^6NC(=O)$ ($C_0$–$C_4$ alkyl)-, $R^6O_2C(CH_2)_{1-4}O(C_0$–$C_4$ akyl)-, $R^6OOC(C_1$–$C_4$ alkoxy), —$R^6OOC(C_0$–$C_4$ alkyl)-, $R^6C(=O)(C_0$–$C_4$ alkyl)-, $R^6C(=O)NR^7(C_0$–$C_4$ alkyl)-, $R^6OC(=O)NR^7$ ($C_0$–$C_4$ alkyl)-, $R^6OC(=NCN)NR^7(C_0$–$C_4$ alkyl)-, $R^6R^7NC(=O)NR^8(C_0$–$C_4$ alkyl)-, $R^6OC(=NC)$ $NR^7$ ($C_0$–$C_4$ alkyl)-, $R^6(CR^{10}R^{11})_{1-4}$ $NR^7C$=O—, $R^6O$ $(CR^{10}R^{11})_{1-4}O$=$CR^7N$—, $NR^6R^7(CR^{10}R^{11})_{1-4}$ C=O $R^7N$—, $R^6O(CR^{10}R^{11})_{2-4}R^7N$—, $R^6O_2C(CR^{10}R^{11})_{1-4}$ $R^7N$, $R^6R^7N$ $(CR^{10}R^{11})_{2-4}R^7N$—, $R^6R^7NC(=NCN)$ $NR^7(C_0$–$C_4$ alkyl)-, $R^6R^7NC(=C(H)(NO_2))NR^7$ ($C_0$–$C_4$ alkyl)-, $R^7R^8N$ $C(=NR^7)$ $NR^7(C_0$–$C_4$ alkyl)-, $R^6R^7N$ $SO_2NR^8(C_0$–$C_4$ alkyl)-, $R^6SO_2NR^7(C_0$–$C_4$ alkyl)-, $R^6R^7N(C_1-C_4)$ CO—, $R^6R^7N(C_2-C_6$ alkyl) O—, $R^6CO(CR^{10}R^{11})_{0-2}$ $R^7N(O_2)S(C_0-C_4$ alkyl), $R^6(O_2)S$ $R^7$ NC(=O) $(C_0-C_4$ alkyl)-, $R^6S(C_0-C_4$ alkyl)-, $R^6S(=O)$ $(C_0-C_4$ alkyl)-, $R^6SO_2(C_0-C_4$ alkyl)-, $SO_2NR^6R^7$, $SiMe_3$, $R^6R^7N(C_2-C_4 alkyl)$-, $R^6R^7N$ $(C_2-C_4$ alkoxy)-, $HSO_3$, HONH—, $R^6ONH$—, $R^8R^7NNR^6$—, $HO(COR^6)N$—, $HO(R^6O_2C)N$, $C_2-C_6$ alkenyl, $C_3-C_{10}$ cycloalkyl, $C_3-C_{10}$ cycloalkylmethyl, aryl$(C_0-C_4$alkyl)-, heteroaryl$(C_0-C_4$alkyl)-, aryl $(C_0-C_4$alkyl)O—, and heteroaryl$(C_0-C_4$alkyl)O—, wherein said aryl groups are substituted with 0–2 substituents independently selected from $C_1-C_4$ alkyl, $C_1-C_4$ alkoxy, F, Cl, Br, $CF_3$, and $NO_2$;

$R^{15}$ is selected from H, halo, cyano, $C_1-C_8$ alkyl, $C_3-C_6$ alkenyl, and $C_3-C_{10}$ cycloalkyl$(C_0-C_4$ alkyl)-, aryl $(C_0-C_4$ alkyl)-, and heterocyclic$(C_0-C_4$ alkyl)-, wherein said aryl or heterocyclic groups are substituted with 0–2 substituents independently selected from $R^{14}$; and $R^{16}$ is selected from H, halo, cyano, $C_1-C_8$ alkyl, $C_3-C_6$ alkenyl, $C_3-C_{10}$ cycloalkyl$(C_0-C_4$ alkyl)-, aryl$(C_0-C_4$ alkyl)-, and heterocyclic$(C_0-C_4$ alkyl)-, wherein said aryl or heterocyclic groups are substituted with 0–2 substituents independently selected from $R^{14}$;

or when $R^{15}$ and $R^{16}$ are on adjacent carbon atoms, or when $R^{15}$ and $R^{16}$ are oriented on the same side of the double bond, as depicted in the following structure (III)

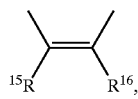

(III)]

$R^{15}$ and $R^{16}$ do or do not form, with the carbon atoms to which they are attached, a 3–7 membered carbocyclic aromatic or nonaromatic ring system, or a 3–7 membered heterocyclic aromatic or nonaromatic ring system, said carbocyclic or heterocyclic ring is unsubstituted or substituted with 0–2 substituents independently selected from $C_1-C_4$ alkyl, $C_1-C_4$ alkoxy, F, Cl, Br, $CF_3$, and $NO_2$;

$R^{17}$ is selected from H, $C_1-C_8$ alkyl, $C_3-C_6$ alkenyl, $C_3-C_{10}$ cycloalkyl$(C_0-C_4$ alkyl)-, $C_1-C_6$ alkylcarbonyl, $C_1-C_6$ alkylsulfonyl, $C_3-C_7$ cycloalkyl $(C_0-C_5$ alkyl)carbonyl, $C_1-C_6$ alkoxycarbonyl, $C_3-C_7$ cycloalkyl$(C_0-C_5$ alkoxy)carbonyl, hydroxy$(C_2-C_4)$ alkyl-, $C_1-C_3$ alkoxy$(C_2-C_4)$alkyl-, $(C_0-C_4$alkyl) $(C_0-C_4$ alkyl) amino$(C_2-C_4)$alkyl-, aryl$(C_0-C_4$ alkyl)-, aryl$(C_1-C_5$ alkoxy)carbonyl, arylsulfonyl, heterocyclic $(C_0-C_4$ alkyl), heterocyclic$(C_1-C_5$ alkoxy)carbonyl, and heterocyclicsulfonyl, wherein said aryl or heterocyclic groups are substituted with 0–2 substituents independently selected from $C_1-C_4$ alkyl, $C_1-C_4$ alkoxy, $C_1-C_4$ alkoxy $C_1-C_4$ alkyl, oxo, F, Cl, Br, $CF_3$, CN, and $NO_2$; and $R^{18}$ is selected from H, $C_1-C_8$ alkyl, $C_3-C_6$ alkenyl, $C_3-C_{10}$ cycloalkyl$(C_0-C_4$ alkyl)-, aryl$(C_0-C_4$ alkyl)-, and heterocyclic$(C_0-C_4$ alkyl), wherein said aryl or heterocyclic groups are substituted with 0–2 substituents independently selected from $C_1-C_4$ alkyl, $C_1-C_4$ alkoxy, F, Cl, Br, $CF_3$, CN, and $NO_2$;

or $R^{17}$ and $R^{18}$, when both are on the same nitrogen atom, may form, with the nitrogen atom to which they are attached, a heterocycle selected from 1-aziridinyl, 1-azetidinyl, 1-piperidinyl, 1-morpholinyl, 1-pyrrolidinyl, thiamorpholinyl, thiazolidinyl, and 1-piperazinyl, said heterocycle may be substituted with 0–3 groups selected from oxo, $C_1-C_6$ alkyl, $C_3-C_7$ cycloalkyl $(C_0-C_4$ alkyl)-, $C_{1-C6}$ alkylcarbonyl, $(C_1-C_6$ alkylcarbonyl)$(C_0-C_4$alkyl)amino-, $C_3-C_7$ cycloalkyl $(C_0-C_5$ alkyl)carbonyl, $C_1-C_5$ alkoxycarbonyl, $C_3-C_7$ cycloalkyl$(C_0-C_5$ alkoxy)carbonyl, aryl$(C_0-C_5$ alkyl), heterocyclic$(C_0-C_5$ alkyl), aryl$(C_1-C_5$ alkoxy) carbonyl, heterocyclic$(C_1-C_5$ alkoxy)carbonyl, $C_1-C_6$ alkylsulfonyl arylsulfonyl and heterocyclicsulfonyl, wherein said aryl or heterocyclic groups are substituted with 0–2 substituents independently selected from $CH_3$—, alkoxy, F, Cl, Br, $CF_3$, CN, and $NO_2$.

2. A compound or pharmaceutically acceptable salt thereof of claim 1 having the formula,

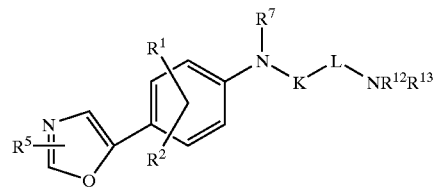

wherein $R_1$ and $R^2$ are each independently selected from the group consisting of H, F, Cl, Br, I, $NO_2$, $CF_3$, CN, $OCF_3$, OH, $C_1-C_4$alkoxy-, and $C_1-C_4$alkyl-;

$R^5$ is selected from the group consisting of H, F, Cl, Br, I, $NO_2$, CN, $CF_3$, $OCF_3$, OH, $C_1-C_4$alkoxy, and $CO_2H$; and $R^7$ is selected from hydrogen and $C_1-C_8$ alkyl.

3. The compound or a pharmaceutically acceptable salt thereof of claim 2 wherein $R^5$ is H;

$R^1$ is selected from the group consisting of $OCF_3$ and $C_1-C_4$alkoxy;

$R^2$ is H; and $R^{13}$ is hydrogen.

4. The compound or a pharmaceutically acceptable salt thereof of claim 3 wherein:

K is C(=O); and

L is C(=O).

5. The compound or a pharmaceutically acceptable salt thereof of claim 4 having the formula,

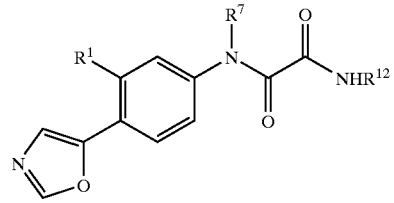

wherein:

$R^7$ is hydrogen;

$R^1$ is methoxy; and $R^{12}$ is $C_1-C_8$ alkyl.

6. The compound or a pharmaceutically acceptable salt thereof of claim 3 wherein:
K is C(=O) and
L is CHR$^9$.

7. The compound or a pharmaceutically acceptable salt thereof of claim 6 having the formula,

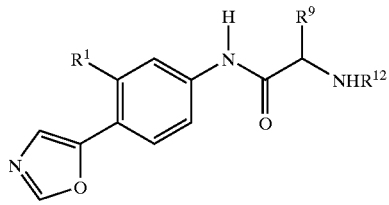

wherein R$^{12}$ is aryl(C$_0$–C$_4$ alkyl)-, said aryl group substituted with 0–3 substituents independently selected from R$^{14}$.

8. A compound or a pharmaceutically acceptable salt thereof of claim 3 wherein:
K is CHR$^9$ and
L is C(=O).

9. A compound or a pharmaceutically acceptable salt thereof of claim 8 having the formula,

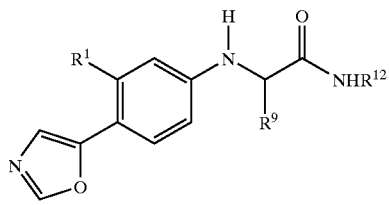

wherein R$^{12}$ is aryl(C$_0$–C$_4$ alkyl)-, said aryl group substituted with 0–3 substituents independently selected from R$^{14}$.

10. A compound or a pharmaceutically acceptable salt thereof of claim 3 wherein:
K is C(=O) and
L is —CR$^{10}$R$^{11}$—(C=O).

11. A compound or a pharmaceutically acceptable salt thereof of claim 10 having the formula,

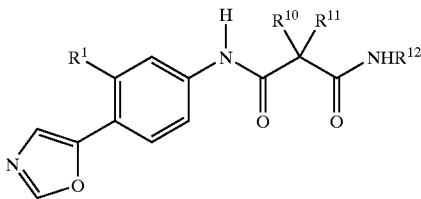

wherein R$^{12}$ is aryl(C$_0$–C$_4$ alkyl)-, said aryl group substituted with 0–3 substituents independently selected from R$^{14}$.

12. A compound or a pharmaceutically acceptable salt thereof, wherein said compound is selected from:
N-(4-Fluorophenyl)-N2-[3-methoxy-4-(5-oxazolyl)phenyl]glycinamide;
N-[3-Methoxy-4-(5-oxazolyl)phenyl]-N2-phenylglycinamide;
N-[3-Methoxy-4-(5-oxazolyl)phenyl]-N2-(3-methylphenyl)glycinamide;
N-[3-Methoxy-4-(5-oxazolyl)phenyl]-N'-phenylethanediamide;
N-[3-Methoxy-4-(5-oxazolyl)phenyl]-N'-(2-methylphenyl)ethanediamide;
N-[3-Methoxy-4-(5-oxazolyl)phenyl]-N'-(3-methylphenyl)ethanediamide;
N-[3-Methoxy-4-(5-oxazolyl)phenyl]-N'-(4-methylphenyl)ethanediamide;
(S)-[[3-[[[[3-Methoxy-4-(5-oxazolyl)phenyl]amino]oxoacetyl]amino]phenyl]methyl]carbamic acid tetrahydro-3-furanyl ester;
N-[3-Methoxy-4-(5-oxazolyl)phenyl]-N'-(3-methoxyphenyl)ethanediamide;
N-[3-Methoxy-4-(5-oxazolyl)phenyl-N'-(phenylmethyl)ethanediamide;
N-(4-Cyanophenyl)-N'-[3-methoxy-4-(5-oxazolyl)phenyl]ethanediamide;
N-[3-Methoxy-4-(5-oxazolyl)phenyl]-N'-(3-methylphenyl)propanediamide;
N-[3-Methoxy-4-(5-oxazolyl)phenyl]-N'-(phenyl)propanediamide;
(S)-[[3-[[3-[[3-Methoxy-4-(5-oxazolyl)phenyl]amino]-1,3-dioxopropyl]amino]phenyl]methyl]carbamic acid tetrahydro-3-furanyl ester;
N-(1,1-Dimethylethyl)-N'-[3-methoxy-4-(5-oxazolyl)phenyl]ethanediamide;
N-[1,1-Bis(hydroxymethyl)propyl]-N'-[3-methoxy-4-(5-oxazolyl)phenyl]ethanediamide;
N-(2-Hydroxy-1,1-dimethylethyl)-N'-[3-methoxy-4-(5-oxazolyl)phenyl]ethanediamide;
N-[[[3-Methoxy-4-(5-oxazolyl)phenyl]amino]oxoacetyl]-2-methylalanine 1,1-dimethylethyl ester;
N-(2-Hydroxy-1,1-dimethylpentyl)-N'-[3-methoxy-4-(5-oxazolyl)phenyl]ethanediamide;
N-[2-[(2-Hydroxy-1,1-dimethylethyl)amino]-1,1-dimethylethyl]-N'-[3-methoxy-4-(5-oxazolyl)phenyl]ethanediamide;
N-[2-(Dimethylamino)-1,1-dimethylethyl]-N'-[3-methoxy-4-(5-oxazolyl)phenyl]ethanediamide;
N-(1,1-Diethyl-2-propynyl)-N'-[3-methoxy-4-(5-oxazolyl)phenyl]ethanediamide;
N-[3-Methoxy-4-(5-oxazolyl)phenyl]-N'-(1,1,3,3-tetramethylbutyl)ethanediamide;
N-(1,1-Dimethylpropyl)-N'-[3-methoxy-4-(5-oxazolyl)phenyl]ethanediamide;
N-[1-(Hydroxymethyl)cyclopentyl]-N'-[3-methoxy-4-(5-oxazolyl)phenyl]ethanediamide;
N-[2-(4-Fluorophenyl)-1,1-dimethylethyl]-N'-[3-methoxy-4-(5-oxazolyl)phenyl]ethanediamide;
N-[[[3-Methoxy-4-(5-oxazolyl)phenyl]amino]oxoacetyl]-α-methyltyrosine methyl ester;
N-[[[3-Methoxy-4-(5-oxazolyl)phenyl]amino]oxoacetyl]-α-methyltryptophan methyl ester;
N-[1,1-Bis(hydroxymethyl)ethyl]-N'-[3-methoxy-4-(5-oxazolyl)phenyl]-N-methylethanediamide;
N-(1,1-Dimethyl-3-oxobutyl)-N'-[3-methoxy-4-(5-oxazoiyl)phenyl]ethanediamide;
N-[3-Methoxy-4-(5-oxazolyl)phenyl]-N'-(1-methyl-1-phenylethyl)ethanediamide;
N-[[[3-Methoxy-4-(5-oxazolyl)phenyl]amino]oxoacetyl]-2-methylalanine methyl ester;
1-[[[[3-Methoxy-4-(5-oxazolyl)phenyl]amino]oxoacetyl]amino]cyclopropanecarboxylic acid methyl ester;

N-(1-Ethynylcyclohexyl)-N'-[3-methoxy-4-(5-oxazolyl) phenyl]ethanediamide; and (R)—N-[1-(Hydroxymethyl)-1-methylpropyl]-N'-[3-methoxy-4-(5-oxazolyl)phenyl]-N-methylethanediamide.

13. A pharmaceutical composition comprising a pharmaceutically acceptable carrier, adjuvant or vehicle and at least one compound of claim 1 or a pharmaceutically acceptable salt thereof, in an amount effective therefor.

14. A pharmaceutical composition for the treatment of an IMPDH-associated disorder, comprising a pharmaceutically acceptable carrier, adjuvant or vehicle and at least one compound of claim 12, or a pharmaceutically acceptable salt thereof, in an amount effective therefor.

15. A method for the treatment of an IMPDH-associated disorder, comprising the step of administering to a subject in need thereof an amount effective therefor of at least one compound of claim 1 or a pharmaceutically acceptable salt thereof.

16. The method of claim 15, wherein said IMPDH-associated disorder is selected from an autoimmune disorder, an inflammatory disorder, a cancer or tumor disorder, a DNA or RNA viral replication disease, and allograft rejection.

17. The method of claim 16, wherein said IMPDH-associated disorder is selected from transplant rejection, rheumatoid arthritis, inflammatory bowel disease, hepatitis B, hepatitis C, herpes simplex type I, and herpes simplex type II.

18. The method of claim 15 further comprising additionally administering one or more of: an immunosuppressant, an anti-cancer agent, an anti-viral agent, an anti-inflammatory agent, an anti-fungal agent, an antibiotic, an anti-vascular hyperproliferation compound, or an IMPDH inhibitor.

19. The method of claim 18 further comprising additionally administering one or more of: another IMPDH inhibitor; a cyclosporin; CTLA4-Ig; an antibody selected from anti-ICAM-3, anti-IL-2 receptor (Anti-Tac), anti-CD45RB, anti-CD2, anti-CD3 (OKT-3), anti-CD4, anti-CD80, anti-CD86, and monoclonal antibody OKT3; an agent blocking the interaction between CD40 and CD154; a fusion protein constructed from CD40 and/or CD154/gp39; an inhibitor of NF-kappa B function; a non-steroidal antiinflammatory drug (NSAID); a gold compound; an antiviral agent; an antiproliferative; a cytotoxic drug; an TNF-$\alpha$ inhibitor; an anti-TNF antibody; a soluble TNF receptor; and rapamycin (sirolimus or Rapamune); or derivatives thereof.

* * * * *